(12) United States Patent
Tarasev et al.

(10) Patent No.: US 8,268,244 B2
(45) Date of Patent: Sep. 18, 2012

(54) APPARATUS TO CHARACTERIZE BLOOD AND RED BLOOD CELLS VIA ERYTHROCYTE MEMBRANE FRAGILITY QUANTIFICATION

(75) Inventors: Michael Tarasev, Pinckney, MI (US); Kenneth Alfano, Canton, MI (US)

(73) Assignee: Blaze Medical Devices, LLC, Ann Arbor, MI (US)

( * ) Notice: Subject to any disclaimer, the term of this patent is extended or adjusted under 35 U.S.C. 154(b) by 0 days.

(21) Appl. No.: 13/204,372

(22) Filed: Aug. 5, 2011

(65) Prior Publication Data
US 2011/0287530 A1 Nov. 24, 2011

Related U.S. Application Data

(62) Division of application No. 12/690,916, filed on Jan. 20, 2010, now Pat. No. 8,026,102.

(60) Provisional application No. 61/146,145, filed on Jan. 21, 2009.

(51) Int. Cl.
*G01N 33/48* (2006.01)
*G01N 33/00* (2006.01)
*G01N 21/00* (2006.01)
*C12Q 1/02* (2006.01)
*C12M 1/34* (2006.01)

(52) U.S. Cl. ... 422/73; 422/68.1; 422/82.05; 422/82.09; 436/63; 436/66; 436/164; 436/522; 435/29; 435/288.7

(58) Field of Classification Search .......... None
See application file for complete search history.

(56) References Cited

U.S. PATENT DOCUMENTS

| | | | |
|---|---|---|---|
| 4,040,742 A | 8/1977 | Jto et al. | |
| 4,178,152 A | 12/1979 | Nunogaki | |
| 4,402,216 A | 9/1983 | Peterson | |
| 4,491,012 A | 1/1985 | Peterson | |
| 4,797,606 A | 1/1989 | Jahn | |
| 7,517,453 B2 | 4/2009 | Bitensky | |

OTHER PUBLICATIONS

Hebert, P. C., Tinmouth, A., and Corwin, H. L. (2007) Controversies in RBC transfusion in the critically ill, Chest 131, 1583-1590.

(Continued)

*Primary Examiner* — Neil N Turk
(74) *Attorney, Agent, or Firm* — Jelic Patent Services, LLC; Stanley E. Jelic

(57) ABSTRACT

The present disclosure describes an apparatus for quantifying the quality degradation of individual stored red blood cell (RBC) units, thereby yielding information to improve decisions regarding their respective allocation, patient suitability, and use. The apparatus for quantifying the quality degradation of individual stored (RBC) units comprises: a hemolysis unit; an optical analysis unit; and a computation unit. This apparatus is amenable to clinical implementation as well as indicative of any given unit's relative viability and thus prospective efficacy. This would provide clinicians with actual data on RBC quality when making decisions about which and how many units to use for transfusion of a given patient. Moreover, deploying this testing throughout the supply chain will improve distribution, planning, and inventory control decisions. A vital aspect of this testing system is the accumulation of copious output and other associated data and the mathematical analyses thereof to optimize algorithms by which to characterize each subsequent test output as meaningfully as possible. While the present invention is directed toward applications in blood quality control, the core technology of "quantifying RBC fragility via stress-induced hemolysis and subsequent optical and computational analysis" could have broader application, such as in disease diagnosis.

16 Claims, 17 Drawing Sheets

OTHER PUBLICATIONS

Shin, S., Ku, Y., Park, M. S., et al. (2005) Slit-flow ektacytometry: laser diffraction in a slit rheometer, Cytometry B Clin Cytom 65, 6-13.

Gu, L., Smith, W. A., and Chatzimavroudis, G. P. (2005) Mechanical fragility calibration of red blood cells, Asaio J 51, 194-201.

Baskurt, O. K., and Meiselman, H. J. (2004) Analyzing shear stress-elongation index curves: comparison of two approaches to simplify data presentation, Clin Hemorheol Microcirc 31, 23-30.

Brandao, M. M., Fontes, A., Barjas-Castro, M. L., et al. (2003) Optical tweezers for measuring red blood cell elasticity: application to the study of drug response in sickle cell disease, Eur J Haematol 70, 207-211.

Tsukada, K., Sekizuka, E., Oshio, C., et al. (2001) Direct measurement of erythrocyte deformability in diabetes mellitus with a transparent microchannel capillary model and high-speed video camera system, Microvasc Res 61, 231-239.

Manabe, Y., Matsushita, N., Kondou, Y., et al. (2000) A new erythrocyte fragility test: a simple procedure utilizing stirring, J Toxicol Sci 25, 161-165.

Hardeman, M. R., and Ince, C. (1999) Clinical potential of in vitro measured red cell deformability, a myth?, Clin Hemorheol Microcirc 21, 277-284.

Dondorp, A. M., Angus, B. J., Chotivanich, K., et al. (1999) Red blood cell deformability as a predictor of anemia in severe falciparum malaria, Am J Trop Med Hyg 60, 733-737.

Huruta, R. R., Barjas-Castro, M. L., Saad, S. T., et al. (1998) Mechanical properties of stored red blood cells using optical tweezers, Blood 92, 2975-2977.

Banerjee, R., Nageshwari, K., and Puniyani, R. R. (1998) The diagnostic relevance of red cell rigidity, Clin Hemorheol Microcirc 19, 21-24.

Gwozdzinski, K., Janicka, M., Brzeszczynska, J., et al. (1997) Changes in red blood cell membrane structure in patients with chronic renal failure, Acta Biochim Pol 44, 99-107.

Dondorp, A. M., Angus, B. J., Hardeman, M. R., et al. (1997) Prognostic significance of reduced red blood cell deformability in severe falciparum malaria, Am J Trop Med Hyg 57, 507-511.

Secomb, T. W., and Hsu, R. (1996) Analysis of red blood cell motion through cylindrical micropores: effects of cell properties, Biophys J 71, 1095-1101.

Wells, J. H., and Singh, R. P. (1989) A quality-based inventory issue policy for perishable foods, Journal of Food Processing and Preservation 12, 271-292.

Lijana, R. C., and Williams, M. C. (1986) The effects of antibiotics on hemolytic behavior of red cells, Cell Biophys 8, 223-242.

Chasis, J. A., and Mohandas, N. (1986) Erythrocyte membrane deformability and stability: two distinct membrane properties that are independently regulated by skeletal protein associations, J Cell Biol 103, 343-350.

Docci, D., del Vecchio, C., Salvi, P., et al. (1985) Osmotic fragility of erythrocytes, cell deformability and secondary hyperparathyroidism in uremic patients on maintenance hemodialysis, Clin Nephrol 23, 68-73.

Fogh-Andersen, N., and Mogensen, F. (1984) On the safety of using stored bank blood for chronic hemodialysis patients, Transfusion 24, 505-507.

Halbhuber, K. J., Feuerstein, H., Stibenz, D., et al. (1983) Membrane alteration during banking of red blood cells, Biomed Biochim Acta 42, S337-341.

Card, R. T., Mohandas, N., and Mollison, P. L. (1983) Relationship of post-transfusion viability to deformability of stored red cells, Br J Haematol 53, 237-240.

Colmer, K., Mostacci, J., Serrallach, E., et al. (1982) Ektacytometry: Instrumentation and Applications in Red Blood Cell Preservation Studies, p. 67, Boston Univ MA School of Medicine, Boston.

Gueguen, M., Durand, F., Cherpi, J., et al. (1981) Filterability and bank blood conservation media, Scand J Clin Lab Invest Suppl 156, 313-316.

Schauf, C. L., Frischer, H., and Davis, F. A. (1980) Mechanical fragility of erythrocytes in multiple sclerosis, Neurology 30, 323-325.

Williams, A. R., Escoffery, C. T., and Gorst, D. W. (1977) The fragility of normal and abnormal erythrocytes in a controlled hydrodynamic shear field, Br J Haematol 37, 379-389.

MacCallum, R. N., Lynch, E. C., Hellums, J. D., et al. (1975) Fragility of abnormal erythrocytes evaluated by response to shear stress, J Lab Clin Med 85, 67-74.

APPARATUS TO CHARACTERIZE BLOOD AND RED BLOOD CELLS VIA ERYTHROCYTE MEMBRANE FRAGILITY QUANTIFICATION

CROSS-REFERENCE TO RELATED APPLICATIONS

This application is a division of application Ser. No. 12/690,916, filed Jan. 20, 2010, now U.S. Pat. No. 8,026,102, which claims the benefit of U.S. Provisional Application 61/146,145 filed Jan. 21, 2009, both of which are incorporated by reference in their entirety. The application also relates to U.S. Non-Provisional Utility application Ser. No. 11/744,643, filed May 4, 2007, which is incorporated by reference in its entirety.

FIELD OF THE INVENTION

The present disclosure is in the technical field of medical apparatuses. More particularly, the present disclosure is in the technical field of quality control of stored red blood cell (RBC) units for the blood banking and transfusion industry.

BACKGROUND OF THE INVENTION

Blood transfusions are used for a wide variety of patients under many circumstances. Most blood transfusions are, in fact, transfusions of red blood cells. Red blood cells are stored in red blood cell (RBC) units. The blood banking industry, transfusion industry, and hospitals monitor RBC units. The current maximum age for transfusable RBC units is 42 days. RBC units are typically administered on a first-in first-out (FIFO) basis.

BRIEF SUMMARY OF THE INVENTION

The present disclosure describes an apparatus for quantifying the quality degradation of individual stored red blood cell (RBC) units, thereby yielding information to improve decisions regarding their respective allocation, patient suitability, and use. This apparatus is amenable to clinical implementation yielding the information indicative of any given unit's relative viability and thus prospective efficacy. This would provide clinicians with actual data on RBC quality when making decisions about which and how many units to use for transfusion of a given patient. Moreover, deploying this testing throughout the supply chain will improve distribution, planning, and inventory control decisions. A vital aspect of this testing system is the accumulation of copious output and other associated data and the mathematical analyses thereof to optimize algorithms by which interpret each subsequent test output to characterize each unit of blood or blood sample as meaningfully as possible. While the present disclosure is directed toward applications in blood quality control, the core technology of "quantifying RBC fragility via stress-induced hemolysis and subsequent optical and computational analysis" could have broader application, such as in disease diagnosis.

The apparatus for quantifying the quality degradation of individual stored RBC units comprises: a hemolysis unit; an optical analysis unit; and a computation unit. Similarly, the associated process for quantifying the quality degradation of individual stored RBC units comprises: a hemolysis step; an optical analysis step; and a computation step.

The hemolysis unit subjects a small sample (preferably from an external strip) from an RBC unit (normally a bag containing 450 ml of RBC) to controlled and varied levels of intensity and/or duration of one or more type(s) of physical stress such as osmotic changes or shear forces.

The optical analysis unit is a spectral analysis unit comprising a light source, a sample block, light dispersing elements(s), and a detector capable of measuring light intensity. The optical analysis unit is able to assess the level of cell free hemoglobin arising due to hemolysis, which occurred as a result of the various stress forces applied to the sample. This hemolysis is indicative of the membrane fragility of the cells in the sample, and thus of the unit sampled.

The computation unit compiles a fragility characterization of the sample and compares the sample to other available units as well as an accumulated body of data resulting from prior testing. The prior testing includes baseline calibration for any given version of the apparatus (to be established and refined throughout clinical validation). The resulting information reflects the relative degradation of a given unit, and can be considered by clinicians or others responsible for allocating or using RBC units.

DETAILED DESCRIPTION OF THE INVENTION

Figure 1:
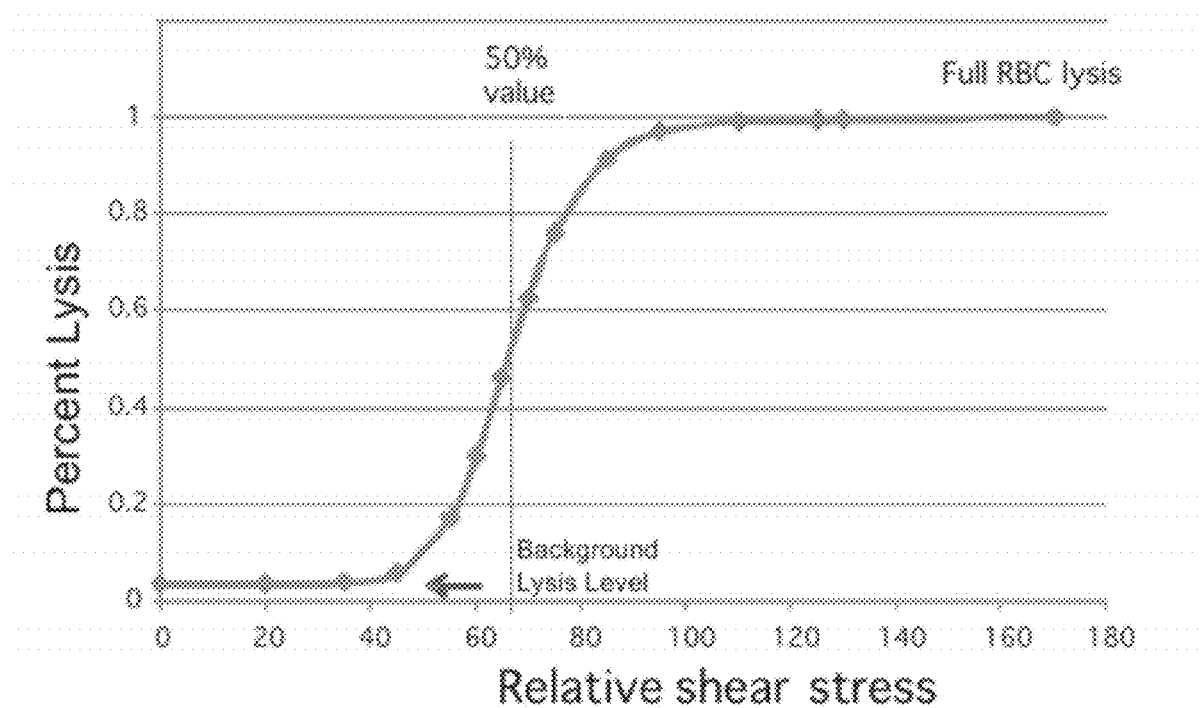
FIG. 1 shows that with a single parameter of total stress magnitude, fragility is conventionally profiled as a sigmoidal function.

During storage, RBC quality degrades due to a number of morphological and biochemical changes in the RBC, including ATP depletion and loss of endogenous RBC antioxidants, leading to damage of RBC cytoskeletal proteins and the membrane in general, resulting in decreased RBC viability in vivo upon transfusion. Such RBC degradation is reflected in the compromised deformability and increased fragility of the RBC membrane, which are negatively linked with post-transfusion RBC survival and tissue-oxygenation efficacy. A more fragile membrane increases any given cell's propensity for hemolysis in vivo and decreases its capacity to deliver oxygen to tissue (even if it survives in vivo).

Research indicates that for certain patient groups (e.g. urgent-care) many RBC units become dangerously ineffective well before their 42-day maximum age. The exact age when this occurs varies among RBC units, and there is currently no means of testing specific RBC units for such loss of viability. The degradation of any given RBC unit varies with several contributing factors in addition to time, including donor to donor variability, storage conditions, and transportation conditions, among others, making the current 42-day uniform age-standard an inadequate proxy.

Extent of degradation is critical for certain patient groups, and if known, physicians could make better informed judgments. For example, critical-care patients are notably harmed by transfusion inefficacy, and thus may warrant priority for the most viable units. However, there is so far no way to discriminate for viability among non-outdated units. Conversely, slowly-degrading units could be acceptable for some patients even beyond 42 days, but without individualized testing, there is no way to identify such units.

With no reliable predictor of transfusion efficacy for any given RBC unit, physicians treating the most vulnerable patients sometimes withhold the transfusions from the patients who they believe can recover without the transfusion (restrictive approach). Such practice can potentially delay patient recovery, increase hospital stays, increase the need for additional procedures, and increase a patient's risk. However, the physician withholding the transfusion may feel that potential complications of using blood with non-reliable viability outweighs the above issues. In other cases, physicians are sometimes forced to use more units than would otherwise be necessary in order to minimize the chance of failing to provide enough viable RBC to restore tissue oxygenation immediately. This not only requires additional units that might have been suitable for other patients, but also subjects the patient to the risk of various complications. (Some risks such as type-match errors are universal and therefore proportional to the number of units being transfused; other complications—like volume overload—are specifically associated with receiving excessive RBC.) In fact, some hospitals currently attempt to accommodate case-by-case requests by trauma surgeons for "fresher" blood. Aside from issues of patient safety and wasted units, there are considerable costs associated with the current practice.

In addition, present methods of blood banking supply chain and inventory management are likewise unable to take into account the degradation rates of particular RBC units, but must instead rely on a "first-in-first-out" (FIFO) system. Lacking a means of measuring and tracking actual quality degradation, the poor proxy provided by time in storage leads to suboptimal routing and distribution.

Red blood cells (also known as erythrocytes) are highly-specialized cells responsible for delivery of oxygen to, and removal of carbon dioxide from, metabolically-active cells via the capillary network. They are shaped as biconcave discs and average about 8-10 microns in diameter. The membrane is very flexible so as to allow the cell to travel capillaries with diameters of only 4-5 microns. At the same time, the membrane must be strong enough to withstand significant ongoing flow-induced stresses while avoiding tears or fragmentation. An erythrocyte with normal membrane stability and plasticity is able to circulate effectively and without damage, whereas a degraded cell is likelier to suffer hemolysis or plug capillaries in vivo.

A variety of anticoagulant and preservative (A-P) solutions have been developed to enable long-term storage. RBC units in liquid state are stored at 1-6° C. with a current maximum FDA-permitted shelf life of 42 days. A significant proportion of patients receive blood products substantially affected by storage. A recent study has shown the average age of RBC transfused in the US to be 21 days. It was reported that in US Army combat support hospitals in Baghdad, the mean storage time of RBC was 33 days. For rarer blood types such as O-Negative, >60% of stored blood units were found to be $\geq$28 days old.

Studies diverge on the question of how the storage time impacts transfusion efficacy. Several preclinical trials link higher storage times to lower tissue oxygenation. Increased storage time has also been implicated in increased incidents of mortality, pneumonia, post-injury multiple organ failure, hemorrheological disorders, serious infections, TRALI, and adverse microcirculatory hemodynamics. Many reviews analyzing the effect of RBC storage on transfusion efficacy raise questions on the risk-benefit profile of using stored RBC in the critically-ill.

On the other hand, a number of studies notably did not detect an adverse effect of RBC storage time on transfusion efficacy. Several hypotheses have been proposed to explain this inconsistency—including insufficient ranges among storage times, the use of mixed/multiple RBC units in any given procedure, the potential effect of white blood cell burden, variable patient physiological conditions, and the idea that storage time alone is a suboptimal indicator of unit viability.

Prolonged storage of RBC results in an array of morphological and biochemical changes, collectively referred as "red cell storage lesion", associated with depletion of ATP and 2,3-diphosphoglycerate (2,3-DPG) levels and increased oxidative stress. Also reported is a decrease in RBC deformability beginning with the end of the first week of storage, a process mediated by storage-induced oxidative injuries and changes in metabolic state. Thus, the condition of the membrane has the capacity to serve as an aggregate indicator of overall cell viability.

The magnitudes of the observed RBC membrane changes appear to depend on a variety of factors besides time, including A-P solution used, the presence of modifying additives, bag material, etc. This issue is further complicated by results indicating that properties of RBC solutions toward the end of their shelf life (including in-vitro hemolysis) were largely dependent upon conditions of production, storage, and/or transport by the manufacturer. This variability may be also related to the presence of other formed elements in the solutions. Variability among RBC properties from different donors adds an additional unknown parameter to degradation levels and/or rates.

RBC deformability loss has been extensively documented by a variety of experimental techniques including micropipette techniques, micropore filtration, optical tweezers, laser-assisted diffractometry (ektacytometry), among others. It should be noted that although in most cases the results are presented and discussed in terms of RC "deformability," the underlying properties measured by these various tests are not necessary identical. Also, some techniques measure properties averaged over all cells in a given sample, while others derive results from a single-cell measurement. While low-stress, single-cell "deformability" tests have long been pursued in clinical diagnostic applications, "fragility" probes cells' propensity for hemolysis under sustained high stresses being applied to an aggregate sample; the latter is expected to better capture the relevant properties for blood quality control applications.

Reduced deformability in RBC has been shown to significantly affect both the post-transfusion survival time in the bloodstream and the cells' ability to traverse the capillary network. Stiffened RBC can significantly alter pulmonary hemodynamics, resulting in increased vascular resistance. Partially-hardened (albeit non-physiologically) cells disappeared from circulation within 25 minutes after transfusion, compared with <2% of others. The study also indicated that reduced RBC deformability leads to cell entrapment in capillaries and microcirculatory blockage, impeding flow through certain regions of microcirculation.

A reduction in post-transfusion RBC viability is a well-established consequence of ex vivo storage. One accepted criterion of transfusion efficacy is >70% RBC survival 24 hours post-transfusion. FDA regulations actually call for this level to be 75%. Currently, this is verified only at the development of the A-P solutions, but compliance is not ascertainable in clinical practice. Tracking post-transfusion RBC survival typically requires radiolabeling, which is only performed in limited research settings. No clinical tests are available to predict the viability of available RBC units.

While there exist various purported means of measuring RBC membrane integrity (fragility and deformability), none has ever been correlated to clinical outcomes, or standardized in a manner conducive to clinical adoption. There is no established "gold standard" of any test or metric for loss of RBC viability. Instead, each metric is defined in terms of its respective testing procedure, with none being established as predicting transfusion efficacy. Most commercial R&D efforts directed at RBC membrane integrity today are focused on low-stress deformability measurement (targeted toward diagnostic applications), rather than high-stress fragility measurement (more likely to correlate with transfusion efficacy.

Notably, the value of developing a test for RBC degradation correlated to clinical utility is presently disputed; some in the blood banking industry currently resist the suggestion that 1) RBC age/degradation is a clinical concern (within the current 42-day limit), or that 2) measuring the degradation of individual RBC units could improve decisions about their use. While data do exist to support both contentions, neither has yet been conclusively established, largely due to the somewhat circular absence of clinically-viable means for the relevant testing. Except for the small sampling of RBC being tested for auto-lysis near outdating (regulated with a 1% maximum in the US), there is presently no systematic assessment of blood product degradation in clinical practice. Moreover, some experts doubt that any in vitro test (including the test for RBC membrane fragility) would be able to predict in vivo cell survival and behavior.

The present disclosure describes the first system for testing the degradation levels of stored blood prior to transfusion that is conducive to clinical adoption and routine use.

The present disclosure describes an apparatus for quantifying the quality degradation of individual stored red blood cell (RBC) units, thereby yielding information to improve decisions regarding their respective allocation, patient suitability, and use. This apparatus is amenable to clinical implementation as well as indicative of any given unit's relative viability and thus prospective efficacy. This would provide clinicians with actual data on RBC quality when making decisions about which and how many units to use for transfusion to a given patient. Moreover, deploying this testing throughout the supply chain will improve distribution, planning, and inventory control decisions. A vital aspect of this testing system is the accumulation of copious output and other associated data and the mathematical analyses thereof to optimize algorithms by which to characterize each subsequent RBC or whole blood unit as meaningfully as possible. While the present invention is directed toward applications in blood quality control, the core technology of "quantifying RBC fragility via stress-induced hemolysis and subsequent optical and computational analysis" could have broader applications, such as in diagnosis of diseases and pathological conditions, monitoring of patient's condition under certain treatments, and assessing and predicting the performance of blood manipulation devices operating both in vivo (e.g. ventricular assist devices or artificial hearts) and ex vivo (e.g. dialysis machines or artificial lungs).

One proposed use for the apparatus is to track the degradation of stored RBC, using membrane fragility as an aggregate metric for ultimate oxygen-delivery capability. Currently, "FIFO" (first-in-first-out) is the most common method of inventory planning Certain deviations from FIFO do exist (e.g. for neonatal patients) but are overwhelmingly based on time in storage as the criteria for anticipate RBC in vivo performance and thus of the transfusion efficacy. However, regularly-performed testing of RBC viability for all units in an inventory would enable a quality-based ranking to supplement (or perhaps eventually replace) time-based ordering and distribution of RBC units. For example, a unit with a higher degradation level and/or rate will get used faster to preempt excessive quality loss; such a proactive practice would minimize overall net degradation before use. Additionally, increased overall viability of RBC units could reduce the amount of units necessary to achieve the same clinical effect of blood transfusion on the patient, thus reducing the overall amount of blood used. Potential also exists for using RBC viability to establish unit expiration times based on actual blood quality, as opposed to a pre-set uniform deadline, thus increasing possible storage time of at least some blood and reducing blood loss through outdating.

Also, if tested near the time of transfusion, a triaging application could enable diversion of low viability units from vulnerable patients and unit selection according to patient efficacy needs to potentially reduce post-transfusion complications and improve overall transfusion efficacy and clinical outcomes. Aside from matching higher-efficacy units with patients who most need them, it could also avoid "wasting" other units on patients whom they may not benefit. For example, it is possible that transfusions which would be deleterious in patients with normal erythrocyte deformability may still be beneficial when performed in patients with markedly altered deformability—particularly for a small oxygen deficit. Clinical trials will establish and refine correlations between transfusion outcomes for various patient types and several RBC fragility-related parameters. Thus, effective triaging may eventually also consider different aspects of blood quality in tailoring unit selections for patient-specific oxygenation needs.

The apparatus for quantifying the quality degradation of individual stored (RBC) units comprises: a hemolysis unit; an optical analysis unit; and a computation unit.

The hemolysis unit subjects a small sample (preferably from an external strip) from an RBC unit (normally a bag containing 450 ml of RBC) to controlled and varied levels of intensity and/or duration of one or more type(s) of physical stress such as osmotic changes or shear forces. Some embodiments of the apparatus may utilize largely established means of achieving the hemolysis step, such as forcing RBC through capillaries. Other embodiments of the apparatus may incorporate proprietary (or, yet additional established) means for either or both elements, depending upon which approach(es) prove(s) to yield the most clinically-predictive results. Moreover, modularization and miniaturization will be pursued in consideration of cost, speed, convenience, versatility, etc. to progressively enhance clinical accuracy and ease of use.

With respect to the hemolysis unit there exist various means of achieving its basic requirements. While these to date by others have been configured to controllably vary only a single aggregate parameter—total applied stress—this component can also encompasses various embodiments configured to control distinct contributing parameters relating to intensity and duration for each type of stress applied.

The core feature of the hemolysis unit is that an RBC sample (small enough to be feasibly obtained under standard medical practices) is precisely and controllably subjected to a range of intensities and/or durations of one or more type(s) of stress. In one embodiment this is done by dividing the sample into many sub-samples, each of which is subjected to a different combination of stress parameters. Alternatively, a sample or subsamples could be subjected to continually escalating parameter levels for real-time analysis at select points. The particular type(s) of stress should ideally correlate as closely as possible with the stress(es) experienced in vivo, subject to other constraints (such as the need for a much wider range of intensities than typically occur in vivo). Such correlations will be verified by substantial clinical testing; early generations of the apparatus will simply use means predicted to yield clinically relevant results.

Note that varying stresses could involve variations in the manner stress is applied, or selected subset(s) of possible changes in or to the nature of the stress(es) being applied. The intensity and duration categories of variable parameters are necessarily quantitative; the stress "type" category may be quantitative, for example, varying an angle of orientation within an apparatus, or qualitative, for example, varying the nature of motion or resistance used to cause the stress. Examples of parameters varying stress intensity include increased pressure forcing the fluid though a capillary, or increased rotational speed if utilizing a gap between concentric cylinders. Examples of parameters varying stress duration include length of time of subjection at a given stress intensity, or number of iterations of some discrete, repeatable action resulting in a given quantum of stress being applied.

Stresses may be used to affect fragility and/or the deformability loss of the RBCs. Note that the stress involved in "fragility" testing is of higher intensity than that involved in "deformability" testing; the former stresses red blood cells in blood samples to the point of hemolysis, while the later provides only limited stress necessary to stretch, or deform, the cells. At this time no fragility test has yet been developed that is both highly-accurate and clinically-feasible.

For purposes of this disclosure, any feature or change of applied stress not attributable to intensity or duration is deemed to pertain to stress "type." Also for purposes of this disclosure, any unqualified reference to "categorical parameters" or "categories of parameters," etc., refers only to those necessarily quantitative parameters of intensity and duration (i.e., does not automatically include type).

The ranges for intensity and duration settings should be such that when both are independently minimized (for any given type of stress), the sample experiences relatively little (ideally 0%) hemolysis, and when both are simultaneously maximized, the sample experiences relatively high (ideally 100%) hemolysis. Importantly, the more (and finer) the gradations for both intensity and duration permitted, the greater the capacity to characterize the sample. (Ideally, the settings for each would be continuous rather than discrete/step-wise, to maximize precision.)

Expected embodiments of the hemolysis unit include at least one stress type with at least one variable parameter for intensity and duration of the stress. Alternative embodiments may have variable parameter(s) for a selected categorical parameter for one or more type(s) of stress. The combination of parameter(s) which are controllable for stress type, intensity, and/or duration will directly influence the computational approach utilized. Preliminary prototypes use off-the-shelf equipment for each component/step, including a commercial bead mill for lysis, a centrifuge and a spectrophotometer for optical measurement. Alternative custom-designed hemolysis units are under development to enable trials with qualitatively different stress types, as it remains unknown which type(s) of in vitro hemolysis will best correlate with in vivo viability. One custom approach employs a system of concentric cylinders, with the inner one rotating to provide cell-wall interaction stress to subsamples residing in the gap. Another employs a capillary-based system utilizing pressure gradient stress as a sample is forced back and forth through the capillary.

One embodiment of the hemolysis unit provides shear stress varying from 0% (not counting in-bag hemolysis) to 100% hemolysis of a given RBC unit sample. Varying the stress magnitude from zero up to the level needed to achieve 100% hemolysis of the sample allows for normalization of observed hemolysis (via free hemoglobin fraction) to the total hemoglobin concentration of each sample, thus giving the fractional hemolysis occurring at each stress gradation.

FIG. 1 shows that with a single parameter of total stress magnitude, fragility is conventionally profiled as a sigmoidal function depicting a 2D representation of RBC membrane fragility profile. A 3D depiction enables graphing lysis dependence upon two selected stress parameters, e.g. intensity and duration. Background lysis is the in-bag "auto-lysis" of RBC, represented at zero applied external stress.

Figure 2:
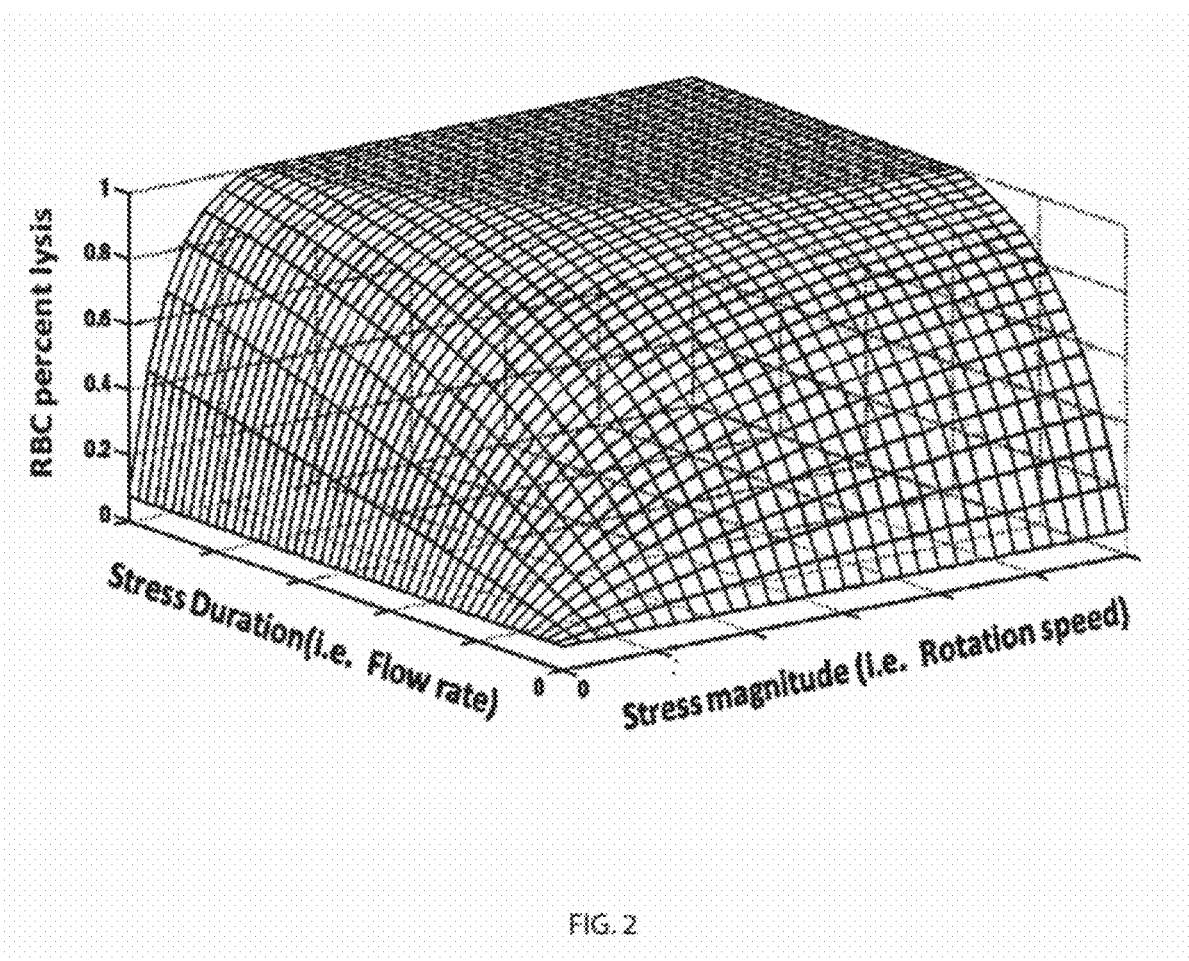
FIG. 2 shows separate parameters of stress intensity and stress duration to create a 3D fragility profile.

FIG. 2 shows separate parameters of stress intensity and stress duration to create a 3D fragility profile. Both parameters contribute to total shear stress, although not necessarily in a direct relationship, so separating them is a feature expected to enhance fragility characterizations. Additional stress parameters may also be added and/or separated for a richer pool of fragility data via higher-dimensional matrices. In addition, RBC membrane fragility measurements can be used in conjunction with other established in vitro tests or assays.

Various complex changes can occur over time or as a result of cell damage or modification due to pathology, decease or anthropogenic influence both chemical and mechanical, to a fragility profile, whether represented as a 3D surface, a higher-dimensional matrix, or any empirically advantageous subset(s) thereof. Such changes could include a change in the mean cell fragility of a sample, a change in the standard deviation for a normally-distributed population, deviations from normality, and/or the development of cell sub-populations with separate distinct profiles. This wide range of potential changes calls for multivariate statistical analyses to generate a comprehensive assessment of any given unit's overall viability or patient-specific suitability.

Ultimately, marketed versions of the apparatus will be fully-integrated systems with permanent benchtop units plus a self-contained disposable cartridge or chip for each unit tested. The disposable portion is where the blood sample will be deposited, and from which the readings will be taken.

Figure 3:
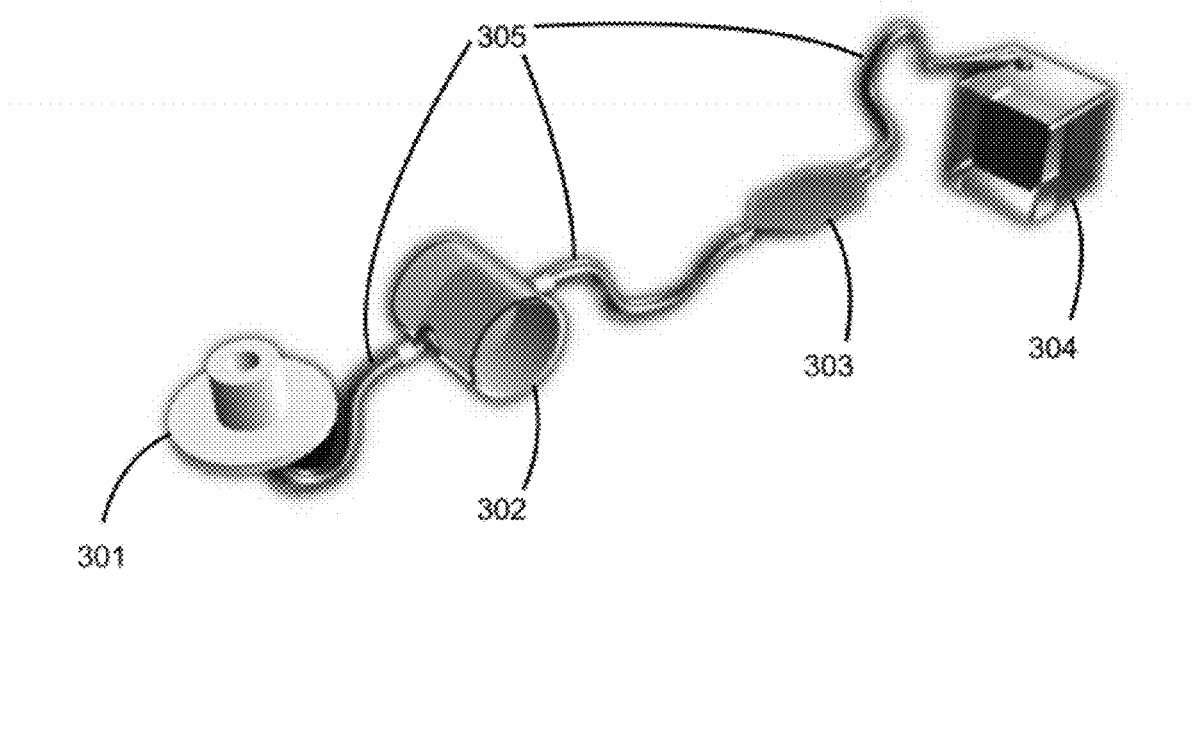
FIG. 3 shows an embodiment of disposable single-use components.

FIG. 3 shows an embodiment of disposable single-use components. A syringe dock 301 is connected to a lysis chamber 302 via tubing 305. The lysis chamber 302 is connected to an optical cuvette 303 via tubing 305. The optical cuvette 303 is connected to a waste reservoir 304 via tubing 305.

Figure 4:
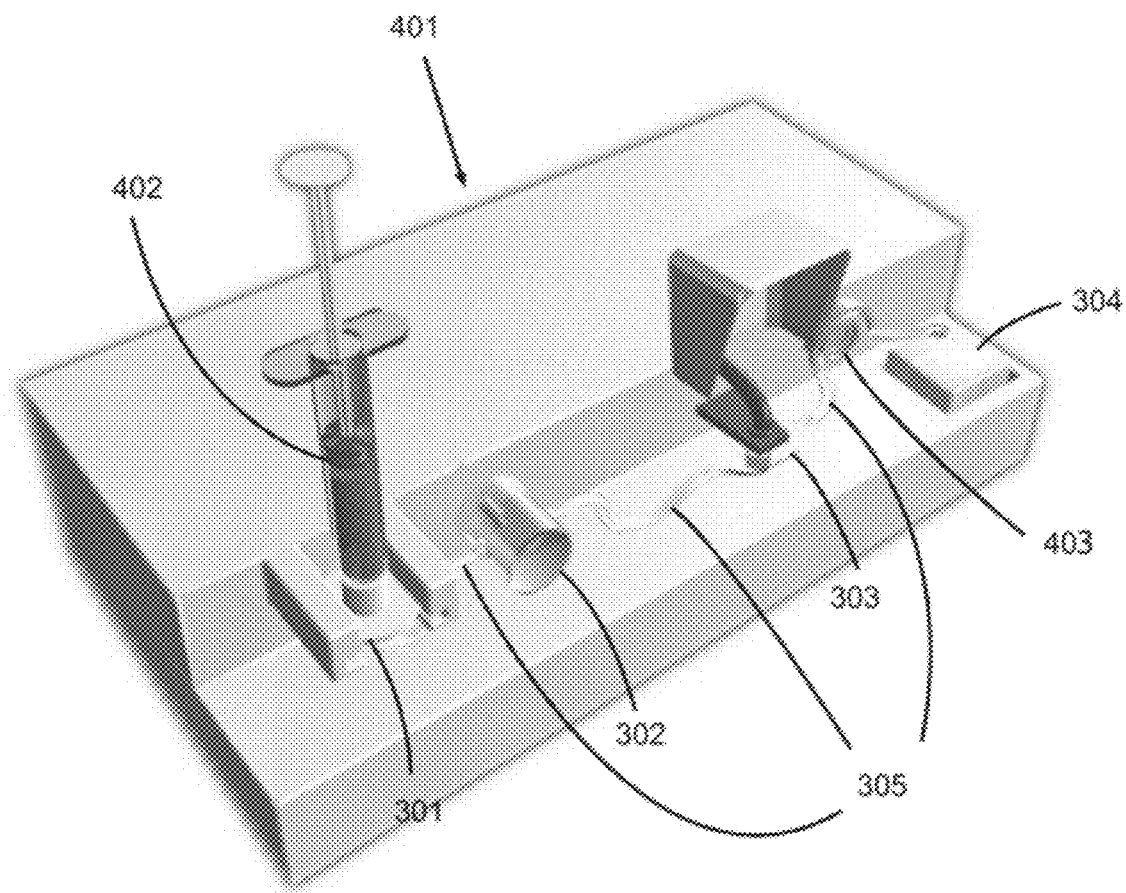
FIG. 4 shows an embodiment of a benchtop apparatus with disposable components attached.

FIG. 4 shows an embodiment of a benchtop apparatus 401. A syringe 402 injects a sample into the syringe dock 301. The syringe dock 301 is connected to a lysis chamber 302 via tubing 305. The lysis chamber 302 is connected to an optical cuvette 303 via tubing 305. The optical cuvette 303 is connected to a waste reservoir 304 via tubing 305. Reduction to a single-use cartridge with components 301, 302, 303, 304, and 305 is anticipated for commercial versions. An integrated peristaltic pump 403 moves sample through the apparatus 401. Not shown are a built-in motor enabling cell lysis and a spectrophotometer enabling analysis of a sample in the optical cuvette 303. The spectrophotometer is connected to the light source and the cuvette via a fiber optic bundle.

The main initial users of the apparatus are expected to be technicians employed in hospital blood banks, who could incorporate it into the battery of tests routinely performed on blood product. Blood bankers and clinicians would decide how to utilize test results for inventory management optimization, patient triage, efficient optimization of blood storage, efficient blood handling methods, improved protocols, and the like.

Published data indicate that beyond the approximately $800 hospitals spend to acquire and transfuse each RBC unit, they spend much more than this on transfusion-related complications)—an often-overlooked cost of transfusion. Hence, any improvement in transfusion efficacy would net significant savings especially considering a relatively modest cost imposed by the testing.

Figure 5:
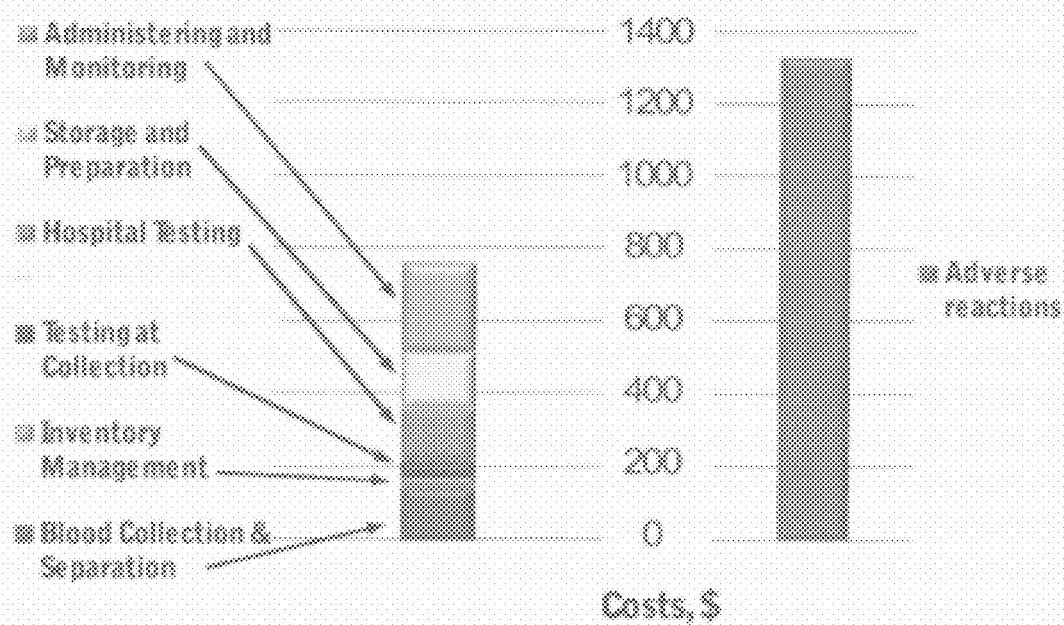
FIG. 5 shows per-unit costs associated with blood transfusions.

FIG. 5 shows a per-unit costs associated with blood transfusions. Hospitals typically acquire allergenic RBC units from the blood banks and blood collection facilities (e.g. Red Cross), at a current cost of about $220 per unit. The cost can be significantly higher for specially-processed RBC products. Hospitals incur additional costs, estimated at $560 per unit, for further blood storage, testing, infusion to the patients, and monitoring the results. These costs could be lower for multiunit transfusions. Hospitals also incur costs associated with treating post-transfusion adverse reactions, owing to both the treatment itself and longer hospital stays. Not included here are costs related to treating transfusion-transmitted diseases, litigation, lost productivity, and burdens on donors. All costs are adjusted for inflation to 2005 dollars.

As noted, the optical analysis unit is a spectral analysis unit comprising a light source, a sample block, and a detector capable of detecting light absorption. The optical analysis unit is able to assess the level of hemolysis which occurred as a result of the various stress forces applied to the sample. This is indicative of the membrane fragility of the cells in the sample, and thus of the unit sampled. Some embodiments of the apparatus may utilize largely established means of achieving the optical analysis step, such as using a commercially-available spectrophotometer. Other embodiments of the apparatus may incorporate proprietary (or, yet additional established) means for either or both elements, depending upon which approach(es) prove(s) to yield the most clinically-predictive results. Moreover, modularization and miniaturization will be pursued in consideration of cost, speed, convenience, versatility, etc. to progressively enhance clinical accuracy and ease of use.

In one embodiment, the optical analysis unit comprises incorporation of the apparatus described in patent application Ser. No. 11/744,643 (Michael Tarasev, inventor). This is one anticipated means for achieving the optical analysis step.

In another embodiment, with minor adaptations, the overall apparatus could be configured to rely instead upon a commercially-available spectrophotometer. Because of the small (sub)sample sizes required, a micro volume spectrophotometer like NanoDrop® (Thermo Scientific) is an example of an appropriate spectrophotometer.

An objective of the optical analysis unit is to determine the proportion of RBC that was lysed (broken up) by the hemolysis unit or step for any given combination of stress parameters applied. Combinations of stress type, intensity, and/or duration parameters will be varied among (sub)samples. This can be done by obtaining a spectral reading for each (sub)sample for which each particular combination of stress parameters was applied and comparing it to the base-line of the pre-stressed sample (0% additional lysis) as well as the (sub)sample exhibiting 100% (full) lysis in which all cells in the sample or subsample are lysed.

The computation unit compiles a fragility characterization of the sample and compares the sample to other available units as well as an accumulated body of data resulting from prior testing. The prior testing includes baseline calibration for any given version of the apparatus (to be established and refined throughout clinical validation). The resulting information reflects the relative degradation of a given unit, and can be considered by clinicians or others responsible for allocating or using RBC units.

With respect to the computation unit, the key is to systematically, thoroughly, and quantitatively characterize each sample according to how susceptible to hemolysis it proved to be under the range(s) of stress parameter(s) applied and measured. Depending on the particular approach and embodiment of the hemolysis unit, there are a number of embodiments of the computational unit possible.

For any embodiment of the hemolysis unit which measures only total applied stress (the common metric presently in the art), or which varies only one parameter (e.g., intensity or duration of a given type of stress, but not both), any given sample shall be characterized by a series of paired values corresponding to the proportion of hemolysis measured by the optical analysis unit to have occurred at each respective stress level.

Figure 8:
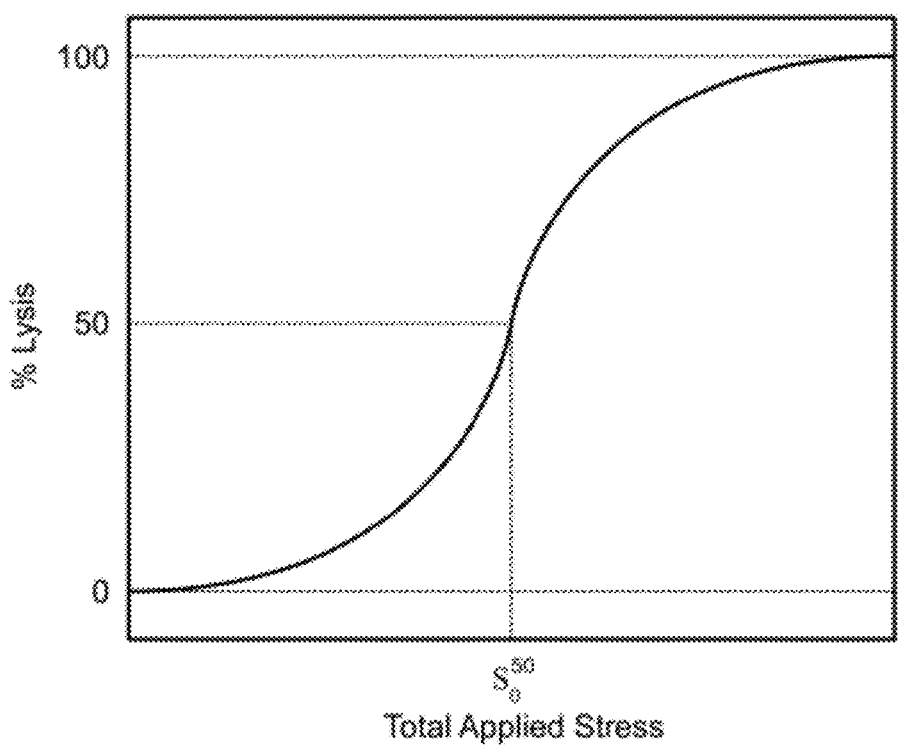
FIG. 8 shows a graphic characterization of a series of paired values corresponding to the proportion of hemolysis measured by the optical analysis unit or step to have occurred at each respective stress level.

FIG. 8 shows a graphic characterization of a series of paired values corresponding to the proportion of hemolysis measured by the optical analysis unit to have occurred at each respective stress level. The graphic characterization is shown as a two-dimensional plot or curve.

For any embodiments of the hemolysis unit with exactly two variable parameters (such as one for each categorical parameter of intensity and duration, for only one type of stress, as expected in early generations), each sample shall be characterized by a 2-dimensional matrix (graphically representable in three dimensions) in which the two dimensions of the matrix represent the two variable parameters. Each constituent element within the matrix represents the proportion of hemolysis (the fraction of cells lysed or of the intact cells that still contain hemoglobin within) measured by the optical analysis unit to have occurred in the hemolysis unit for that particular combination of both applicable parameters. (Significant interdependence is expected, as for any given type of stress the effect on RBC at any given intensity will be greater at longer durations, and vice versa; having at least two dimensions to the characterization is expected to provide a more textured and complete characterization upon which to base predictive models of prospective sample viability.)

For any embodiments of hemolysis unit with more than two (number n) variable parameters (via any number of different stress types, intensity-parameters, and/or duration-parameters), each sample shall be characterized by a matrix with greater than two (n) dimensions (not directly graphically representable; indirectly depictable via hypercubes, multiple 2-D and/or 3-D plots, etc.). Each dimension of the matrix represents a variable parameter (under exactly one category of stress type, intensity, or duration), of which there could be several for any or all of the three categories. Each element within the multi-dimensional matrix represents the proportion of hemolysis measured by the optical analysis unit or step to have occurred in hemolysis unit or step for that particular combination of all applicable parameters.

Combinations of parameters which include variable type(s) of stress must ensure that any possible changes in stress type are compatible with all other variable parameters designated to be varied concurrently. It is also possible that changing one parameter may alter the meaning or significance of another, which may or may not be acceptable in any given case. (For example, varying a given kind of intensity may conceivably have an implicitly integral impact on a given duration metric, or vice-versa.) Moreover, there is no requirement that all elements, vectors, plane arrays, or other subsets of any characteristic matrix be complete for any given combination of possible parameters. (For example, a hypothetical cubic matrix representing exactly one parameter under each category of type, intensity, and duration may find certain values for duration being incompatible with certain ranges of intensity; alternatively, a given stress type may only be compatible with varying duration but not varying intensity.) Hence cubic matrices could have planar slices missing; hypercubic matrices could have cubes missing, etc. In another example scenario, each type of stress could potentially require its own unique set of intensity/duration parameters (incompatible with those of all other types). For any such circumstances, the empirical analysis of the data accumulated, utilizing established mathematical (i.e., statistical, numerical) methods will ultimately determine the value of any (sub)combinations.

Expected empirical trends upon which to base predictive models (and thus computation of test-sample characterization) include any combination, subset, or relative prominence of the following: i) changes in proportion of hemolysis occurring prior to any deliberate subjection to stress ("base-line" lysis or "auto-lysis," reflected in proportion of hemolysis with zero stress applied); ii) changes in "mean" fragility (reflected in stress parameter combinations necessary to achieve 50% hemolysis), iii) changes in the overall distribution of fragility across sample RBC (reflected in the spread or distribution of lysis occurring across the range of stress parameters applied), such as an increase in the standard deviation of a 2-D fragility profile, iv) non-uniform or asymmetrical changes in RBC sample fragility, such as with a boundary-effect from base-line lysis, and v) various combinations of the above for sub-populations of RBC in any given sample, such as from varying times of withdrawal from circulation. For any of these or other observed correlations to clinically-relevant data, sophisticated statistical modeling may be employed to construct a robust characterization of each prospective sample in view of such established correlations.

Figure 9:
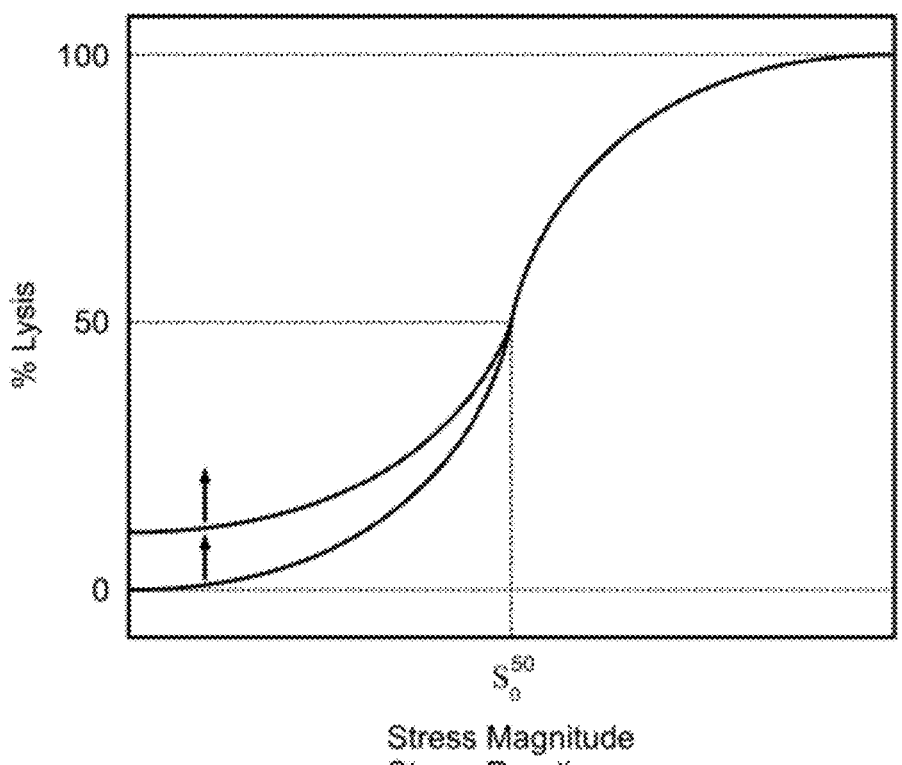
FIG. 9 shows a change in the baseline of RBC lysis.

FIGS. 9 through 14 represent examples of hypothetical samples' observed changes in 2D fragility profiles or curves and thus implicitly for prospective higher-dimensional profiles of RBC fragility. These changes can occur independently of each other and thus can simultaneously affect the observed fragility profile, thereby generating an experimentally-observed profile with attributes comprising a multitude of elemental changes as discussed/shown here:

FIG. 9 shows a change in the baseline of RBC lysis. Such a change reflects the amount of cell-free Hemoglobin (Hb) in RBC solution. In vivo levels of free Hb are typically low, however such levels are known to increase due to blood manipulation during its collection from donors. As mentioned, increased cell free Hb has been documented to occur during RBC storage and relates to RBC auto lysis during storage.

Figure 10:
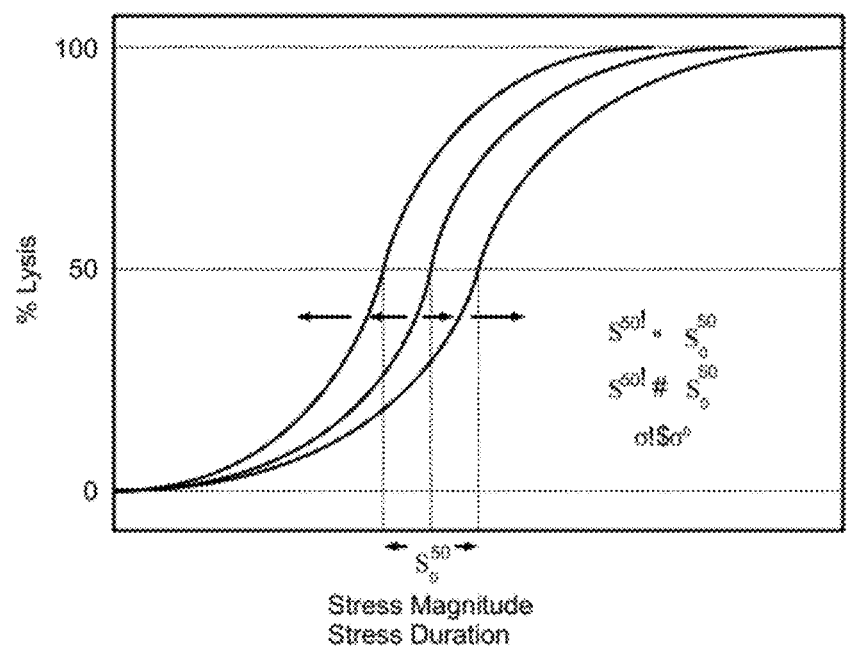
FIG. 10 shows a shift of the stress curve.

FIG. 10 shows a shift of a stress curve (S-curve). If the mean fragility value changes, the S-curve will shift along the stress axis. Examples are: the stress level determined as duration necessary to lyse 50 percent of the cells at a given stress magnitude; or a magnitude necessary to lyse 50 percent of the cells at a given stress duration ($S_o^{50}$) changes while the distribution profile (given as, for example, the standard deviation of such a distribution: $\sigma$) remains unchanged. Existing data suggest that for RBC storage this shift can be expected to be towards lower total stress levels, indicating a change in membranes that makes them more rigid (less flexible) and thus less able to withstand applied stress.

Figure 11:
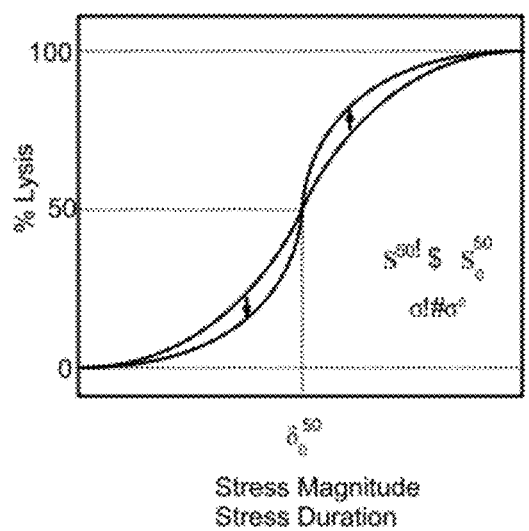
FIG. 11 shows a symmetrical increase of the slope of the S-curve.

FIG. 11 shows a symmetrical increase of the slope of the S-curve. If the mean fragility of the cells remains unchanged, but the distribution of fragilities of the cell population changes (e.g., becomes more or less homogeneous) a change in the slope of the S-curve is expected. Such change reflects a change in the fragility distribution profile (e.g., $\sigma$) while the mean value (e.g., $S^{50}$) remains unchanged.

Figure 12:
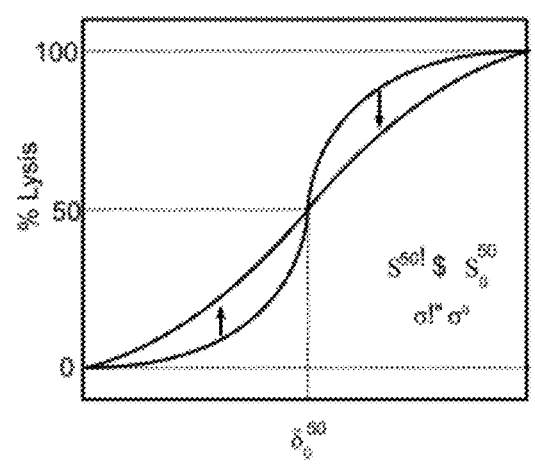
FIG. 12 shows a symmetrical decrease of the slope of the S-curve.

FIG. 12 shows a symmetrical decrease of the slope of the S-curve. If the mean fragility of the cells remains unchanged, but the distribution of fragilities of the cell population changes (e.g., becomes more or less homogeneous) a change in the slope of the S-curve is expected. Such change reflects a change in the fragility distribution profile (e.g., $\sigma$) while the mean value (e.g., $S^{50}$) remains unchanged. It is anticipated that cell aging and longer storage time would result in increased values of standard deviation of RBC fragility profiles, resulting in less-vertical slopes.

Figure 13:
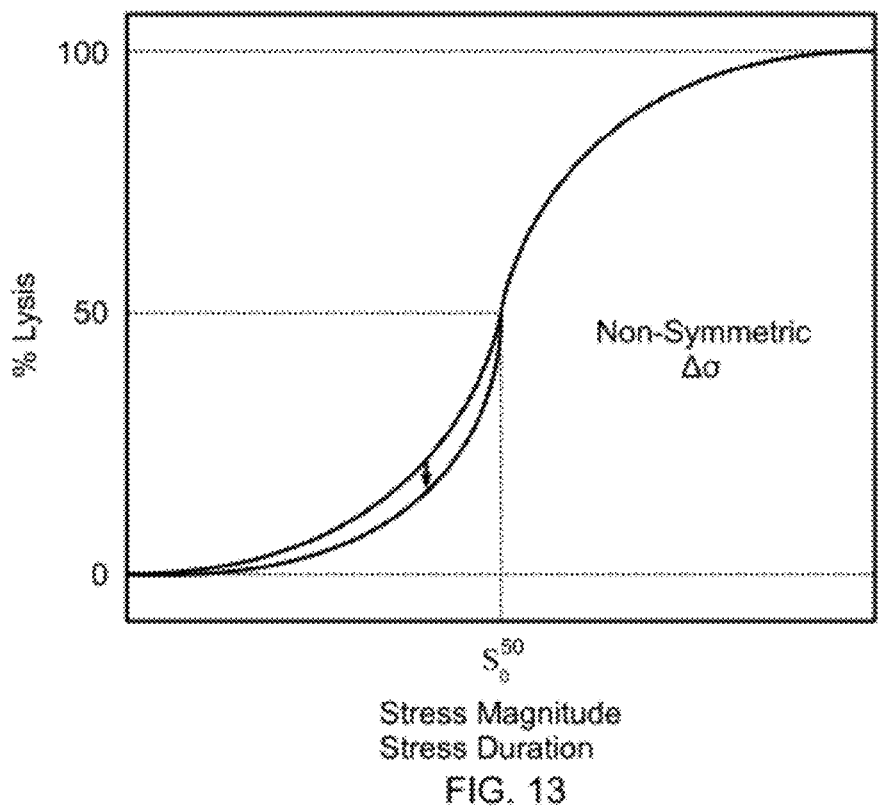
FIG. 13 shows an asymmetrical change of the slope of the S-curve.

FIG. 13 shows an asymmetrical change of the slope of the S-curve. Changes in the distribution of individual fragilities of RBC may not affect the whole RBC population uniformly, and thus can result in asymmetrical changes in the fragility distribution profile. For example, the distribution of cell fragilities may become asymmetrical due to a boundary effect of cell auto-lysis (lysis at zero stress).

Figure 14:
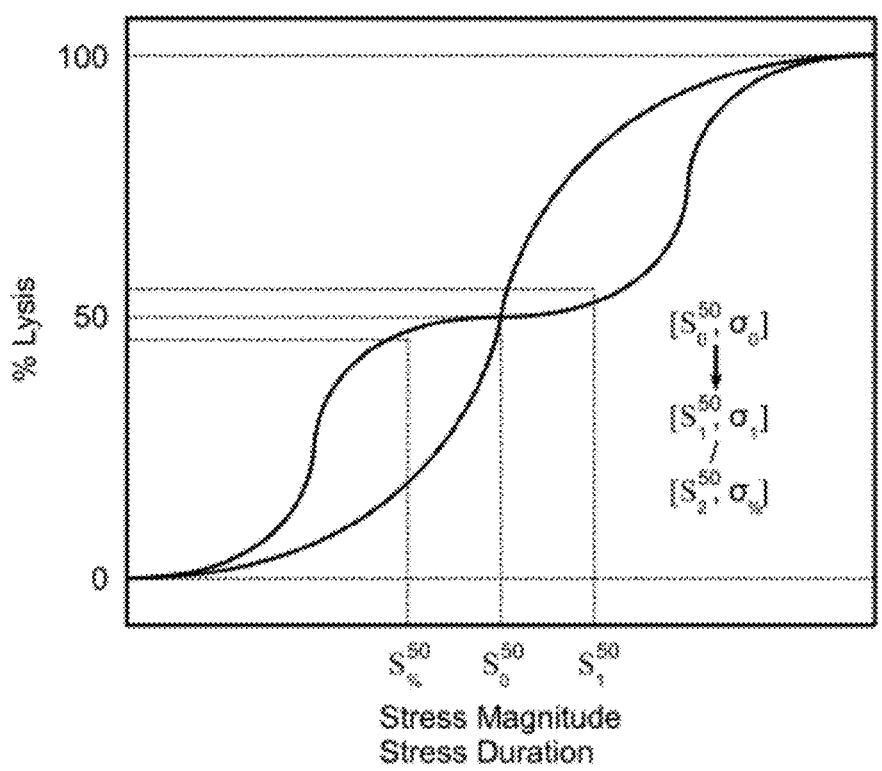
FIG. 14 shows a change from a single S-curve to two S-curves arising from two RBC populations.

FIG. 14 shows a change from a single S-curve to two S-curves arising from two RBC populations. While a common RBC population in solution can be adequately described by a fragility profile (e.g., defined by mean and standard deviation), changes in RBC membrane fragility can potentially be different for various sub-populations of RBC (e.g., following changes in morphology or reflecting relative RBC age at the time of cell withdrawal from donor's circulation). The development of two or more sub-populations with significantly different fragility profiles would result in the observed profile exhibiting "multi-phase" or "multi-curve" properties.

The anticipated, iterative sequence of implementation for this testing system is to clinically validate by simultaneously taking measurements in the manner described above while tracking one or more metric of clinical outcomes of transfused patients, as well as which RBC units they each receive. Based on the clinical outcomes and the respective characterizations of all corresponding samples, candidate models are constructed for correlating the latter to the former. Ultimately, a method of processing all available characteristic data for each sample is chosen to generate some predefined value or set of values for each sample representing its unit's viability for prospective transfusion. Note that this value only represents RBC viability (and thus prospective efficacy); clinicians must then translate such relative values into determinations of which units are acceptable or preferable for selected patients under various circumstances. (Similarly for supply or inventory management, blood bankers would use professional judgment in their decisions based upon the test output data.) Recursively, such professional judgments should only improve with time as the testing becomes more established and routine in clinical practice.

The advantages shown in the present disclosure include (without limitation) allowing clinicians to ascertain the severity of degradation of any stored RBC unit near its point of use, and informing medical judgments for optimally allocating typically-scarce units. For the first time, clinicians would know the viability and expected efficacy of each RBC unit before deciding whether to use it for a particular patient. For those patients requiring especially high efficacy—such as trauma surgery—this means that patients may receive blood transfusions while at present, under restrictive protocol, they would not get one thus allowing for faster and easier recovery and shorter hospital stays. In other cases, less blood would be required, as in the practice of transfusing additional units in an attempt to compensate for the inadequate unit viability or for unknown and intolerable risk of inadequate performance. Hence, the risks of complications associated with excessive transfusion will likewise be attenuated. Costs of the additional units, their transfusion, and medical care for the noted complications will also be reduced. Furthermore, there is research to suggest that for some patients, receiving a blood product of suboptimal efficacy can directly cause harm. Moreover, this metric will be useful not only near the point-of-use, but also throughout the supply chain and distribution channels to optimize inventory planning and control. Instead of the first-in-first-out (FIFO) system, units can be strategically routed based on real-time data on their respective anticipated viability and measured degradation rates (utilizing established supply-chain and inventory management tools); this will improve the aggregate utilization of a scarce and uncertain blood supply. In all such considerations, the degree of ability to precisely characterize blood product degradation via RBC fragility quantification is proportional to the potential for efficient triage of limited inventories.

Further advantages involve the high-stress (fragility) based approach to determining RBC membrane plasticity, in contrast with the prevailing low-stress (deformability) based approaches used by others devising related tests for clinical diagnostic purposes. While the two resulting metrics are likely correlated, applying high-stress (i.e., deliberately inducing hemolysis) is potentially more correlatable to physiological hemolysis in vivo and transfusion efficacy. Moreover, it may be more conducive to the development of extensive, efficient, and/or multi-parameter data collection and analysis protocols, robust, standardized, and/or readily-usable blood products. Such considerations are also relevant to additional applications beyond the primary objective of blood quality control, such as certain diagnostic markets.

While these descriptions of the invention enable one of ordinary skill to make and use what are considered presently to be the best modes of every respective aspect thereof, those in the field will also understand and appreciate the existence of variations, combinations, and equivalents of the specific embodiments, methods, and/or examples used. Many variations in form and uses would occur to those skilled in the art. Potential variations include various alternate means of subjecting the RBC sample to stress, or of quantifying how much hemolysis occurred after subjecting the sample to said stress. Other variations may alter the index or value assigned to the test results. All such and other variations are intended to be within the scope and spirit of the invention and are further illustrated in the following examples.

EXAMPLE 1

Steps to Improve Utilization of RBC Units in a Clinical Setting (Non-Exhaustive)

1. Assess the actual fragility properties of RBC units. Such an assessment, includes the determination of the differentiation of actual fragility profiles of a stored (aged) RBC unit from that of freshly-drawn RBC. Such a profile will be constructed along at least one dimension of parameter(s) which contribute to RBC lysis which can encompass varying intensities and/or durations of stress as well as different methods of applying shear stress such as cell-wall interaction, external mechanical pressure variation, osmotic shear stress, or other physical stresses.
2. Correlate the actual fragility properties of RBC with anticipated performance characteristics of RBC in-vivo. Performance characteristics to be derived from the evaluation of fragility profiles could include, but are not limited to:
    Anticipated RBC survival levels in the bloodstream after the transfusion
    Anticipated time dependence of the fraction of cells able to traverse the capillary network and thus presumably deliver oxygen to the tissues
    Anticipated rate of lysis of RBC in-vivo
    Initial level of cell free hemoglobin
3. Correlate the anticipated performance characteristics of each RBC unit with optimal specific requirements for the transfusion for each clinical condition. Specific requirements related to clinical conditions may include:
    Initial level of active RBC in the unit
    Initial level of cell-free hemoglobin in RBC unit
    Required short-term survival of RBC after the transfusion
    Required long-term survival of RBC after the transfusion (expressed as a rate of transfused RBC degradation/lysis)
4. Select and transfuse to each patient RBC units with anticipated performance characteristics most closely correlated to optimal specific requirements of each patient's clinical condition. Although it is desirable that for each clinical condition transfused RBC perform the same as healthy native RBC of the patient, attainment of such a goal is not feasible in current medical practice. Thus it is desirable to optimize the overall efficacy of the transfusion in such a way so each patient derives the maximum possible benefit from each RBC transfusion.

EXAMPLE 2

Implementing the Steps from Example 1 for Selected Patient Conditions

Selecting RBC units for the transfusion taking into account the specific requirements of particular patient groups (on the example of acute care patients and sickle-cell anemia patients). While the use of the best and the most efficacious RBCs is preferential for all patients regardless of the condition, the necessity of blood storage combined with the needs of blood distribution and allocations creates the need for triaging of the blood supply based on specific patient needs. The matching of RBCs with specific identified and/or anticipated membrane fragility properties with pathological conditions having pre-determined specific requirements for fragility properties of RBC considered for transfusion can be demonstrated on a sample case of acute blood loss in a trauma patient.

The main requirement for transfusion efficacy in a trauma patient is immediate and efficient restoration of the oxygen-carrying capacity of his blood. At the same time, there is potentially room to compromise if necessary on the long-term survival of RBC in the bloodstream (long-term oxygen carrying capacity of transfused RBC). In the case of acute blood loss in trauma, the oxygen delivery to the tissues must be restored as soon as possible to avoid irreversible tissue damage or patient death. At the same time, as long as the transfusion effects immediate restoration of blood oxygen-carrying capacity, it is of relatively less importance how long the transfused cells would remain intact and active within the patient. Thus, a unit able to maximally restore immediate oxygen carrying capacity may be deemed acceptable even if (hypothetically) all transfused RBC will be removed from circulation after the first 24 hours following the transfusion. Barring volume overload complications, such a patient may be transfused with additional units if necessary to alleviate anemia symptoms.

Sample requirements related to this particular condition (trauma victim):

Minimal free hemoglobin in the sample to reduce potential free-hemoglobin-related nitrous oxide (NO) depletion associated with vasoconstriction;

Maximum amount of active (able to deliver oxygen/traverse capillary network) RBC at time zero (time of transfusion);

Maximum short-term (i.e., 24 hours) RBC survival rate.

Figure 15:
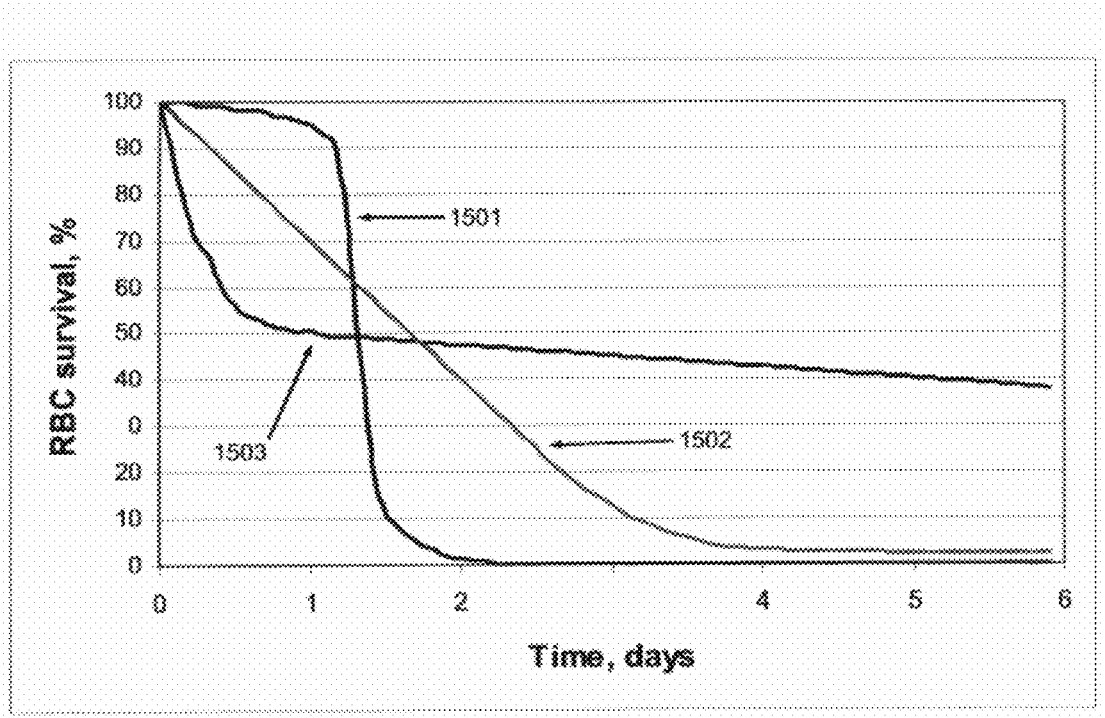
FIG. 15 shows the time-dependence curve of RBC percent survival at a given shear stress intensity.

These are then correlated to appropriate anticipated performance characteristics of available RBC units. For example, FIG. 15 shows the time-dependence curve of RBC percent survival at a given shear stress intensity. This situation may be represented by any of the three scenarios. While samples exhibiting the properties represented by both Curves 1501 and 1502 would both be acceptable based on current FDA standards, the sample represented by Curve 1501 would be preferred in the above case. (Alternatively the sample represented by Curve 1503 could potentially be preferred for sickle-cell anemia (see example below), where instead long-term RBC survival is of primary consideration.

Long-term support of oxygen delivery would be the primary requirement for the transfusion in another example: sickle-cell anemia patients. Depending on the condition, such patients may exhibit symptoms of severe anemia, which can be relieved by a blood transfusion. In more severe cases, over 50 transfusions per year may be required. Clearly, the duration of transfused RBC survival in patients' blood stream is of critical importance here. At the same time, the initial (immediately after the transfusion) contribution to tissue oxygenation may be of secondary importance—in marked contrast to trauma victims. For example, it can be envisioned that for a sickle-cell anemia patient a unit with 50% active RBC and a long in vivo life span expectancy (Curve 1503 on FIG. 15), though unacceptable by current FDA standards, might actually be preferable to a unit with 100% active RBC at the time of transfusion but with a much shorter life span (i.e., as depicted on Curve 1501 on FIG. 15), which by exhibiting less than 25% reduction in RBC count in the bloodstream after the first 24 hours would be acceptable by the current FDA standard. Of course, much improvement in blood allocation can be achieved even without altering FDA standards, but the potential for individualized tailoring and triaging could indeed make such changes warranted in the future.

In the above example, significantly higher stability exhibited by a fraction of RBC population (as in Curve 1503, FIG. 15) allows for about 3.5× higher total oxygen delivery over the first week, as represented by the area under the respective curves, and about 8-fold higher delivery over the first month, compared to RBCs with membrane fragility profiles depicted on Curve 1501 on FIG. 15. This is aside from the patient's need for a steady oxygen supply—something that is not possible with RBC that exhibit degradation as shown on Curve 1501 on FIG. 15. At the same time, taken over the first 24 hours, transfusion of an RBC unit with properties as in Curve 1501 can be expected to deliver about 40 percent more oxygen to the tissues as the those with properties as in Curve 1503, providing a much stronger short-term benefit to the patient. While these examples may take potential case scenarios to a deliberate extreme, they underscore the concepts, problems, and potential solutions in real-life RBC transfusion.

Other pathological or clinical conditions would impose similar constraints on the ability of RBC to survive and perform their function in vivo after transfusion. As shown by the examples above, various cases can be envisioned to place different emphasis on magnitude of the oxygenation boost provided by the transfusion or the time changes of such an oxygenation boost. Consequently, different RBC survival requirements would relate to different parameters of in vivo stress that RBCs are subjected to. The rapid oxygenation boost necessary for a trauma patient would emphasize the ability of RBCs to withstand high initial stress (featuring stress intensity parameters/dimensions of any characterization more prominently), while placing a lower premium on a cell's ability to withstand long-term, low-level stress (featuring less prominently those parameters pertaining to duration). At the same time, sickle cell anemia patients who benefit from long-term cell survival would benefit from RBC ability to withstand low-intensity stresses at longer durations.

Preceding example demonstrates that a significant possibility exists to triage blood supplies by tailoring transfusions (or the fragility profiles of the RBC to be transfused) to particular requirements and needs of various patient population groups.

The approach to determination of RBC fragility through the means detailed in this invention was preliminarily tested using a commercially available bead mill (TissueLyser LT from Quiagen), and a NanoDrop ND 100 spectrophotometer. The TissueLyser subjects a sample to shear stress with variable parameters of oscillation frequency and duration. While custom lysis units and a proprietary optical unit remain under development, this pilot system enables convenient benchtop testing of fundamental concepts.

Figure 6:
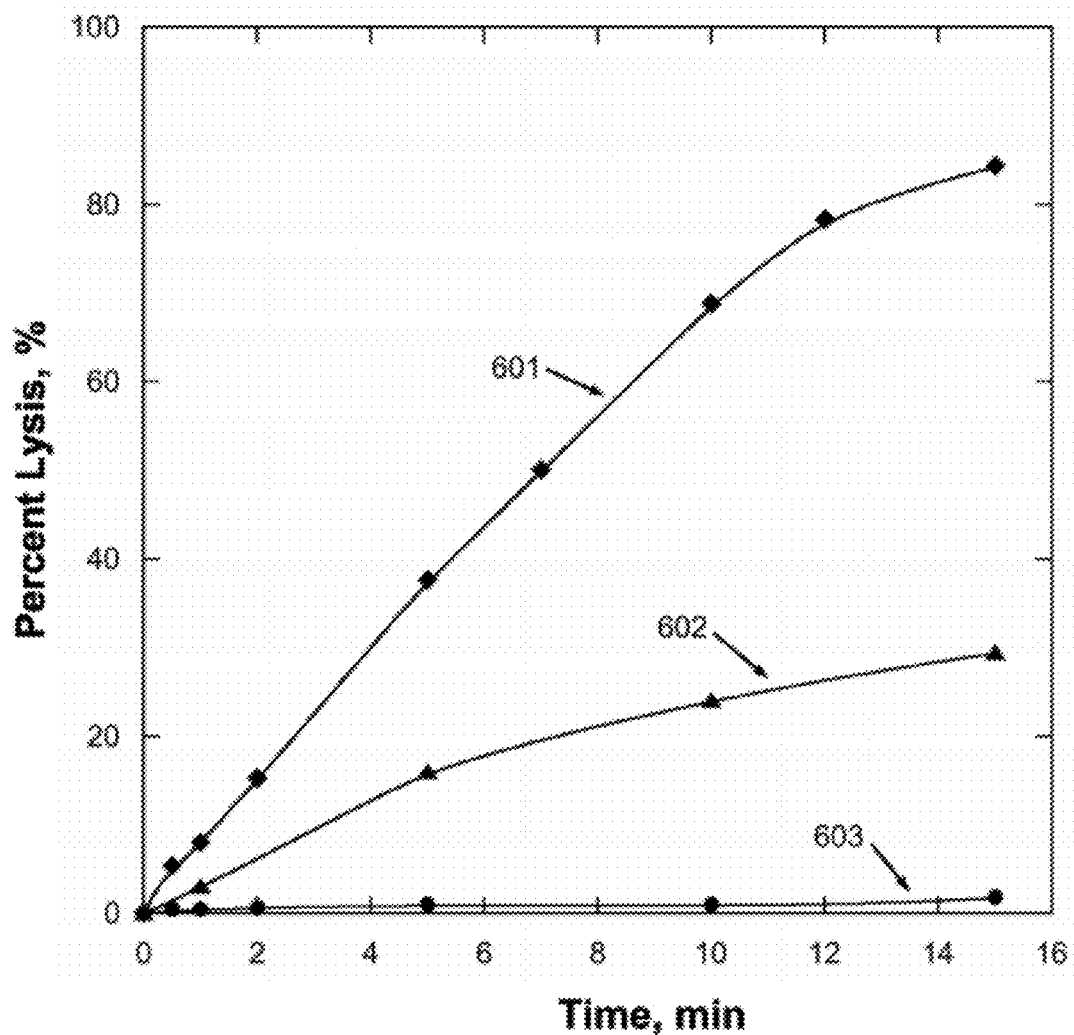
FIG. 6 shows dependence of induced RBC lysis upon shear stress duration and intensity.

FIG. 6 shows dependence of induced RBC lysis upon shear stress duration and intensity. Undiluted RBC samples of 1.5 ml obtained from one unit (21 days before expiration) were each lysed using a TissueLyser LT (Quiagen) with a single 5 mm steel bead. Samples were lysed at three different oscillation frequencies: 50 Hz 601, 35 Hz 602 and, 15 Hz 603. After brief centrifugation, aliquots of supernatant were diluted as needed with 0.1M HEPES, pH 7.8, and the amounts of released hemoglobin (Hb) were measured using a NanoDrop ND 100 spectrophotometer based on the $A_{577}$-$A_{700}$ absorbance difference. Results are presented as fractions (percent lysis) of Hb released into the supernatant compared to known total Hb content as determined via repeated freeze-thaw of a sample using liquid nitrogen. As anticipated, higher stresses resulted in greater lysis as reflected in the resultant concentrations of free hemoglobin. Arrays of 2D profiles similar to those in FIG. 6 could be used to construct 3D profiles, as described above.

Figure 7:
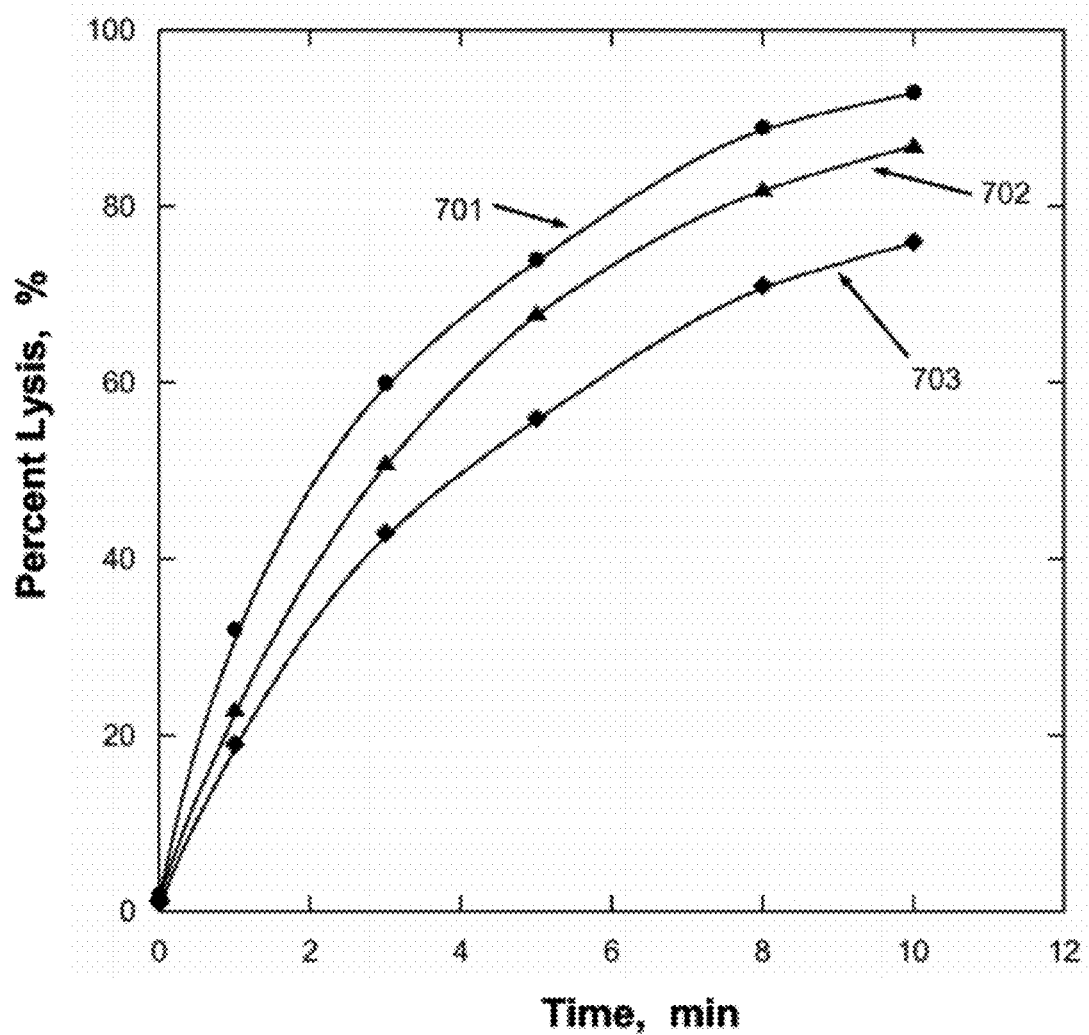
FIG. 7 shows preliminary data obtained from three RBC units of the same age and before expiration.

FIG. 7 shows preliminary data obtained from RBC units of the same age and before expiration. Out the six units tested, three units are shown as curves 701, 702, and 703 respectively. The lysis step used varying stress durations with a fixed intensity of 50 Hz. Results indicate that among 6 randomly-selected RBC units of the same age, there was statistically significant variability in cell fragility which was reproducibly detected by the described approach.

For FIG. 7, RBC samples obtained from unit test strips (10 days before expiration) were diluted prior to lysis to 25 µM total hemoglobin concentration with AS3 storage solution supplemented with 30 g/L bovine serum albumin. Lysed samples were 350 uL, and no post-lysis dilution was performed. Otherwise, lysis and subsequent spectral analysis were conducted similarly to FIG. 6. Each data point represents 3 independent measurements; the average $\sigma$=4%, excluding measurements at "zero" duration (representing in-bag lysis) for which $\sigma$=10%.

Figure 16:
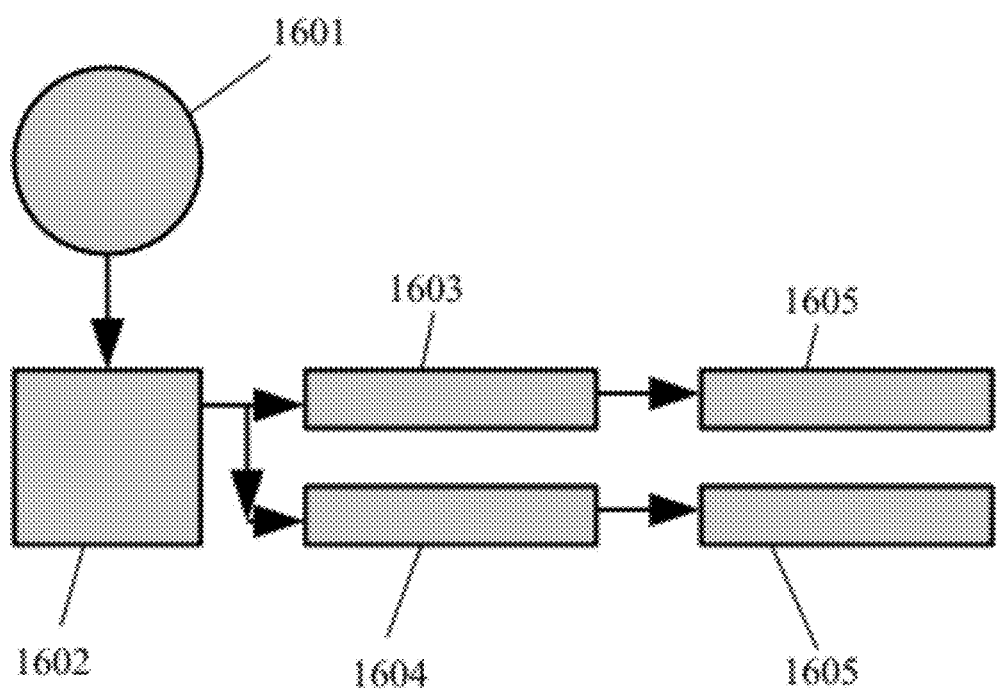
FIG. 16 shows a block diagram of a generalized spectrophotometer as an example for the optical unit.

FIG. 16 shows a block diagram of a generalized spectrophotometer, which is capable of optically evaluating hemolysis, as an example embodiment of the optical unit. This optical unit comprises a light source 1601 which directs light into a monochromator 1602. The monochromator outputs light with a narrow wavelength which is split and passed through a reference 1603 and sample 1604. Detectors 1605 determine transmissivity for both the reference 1603 and sample 1604.

Figure 17:
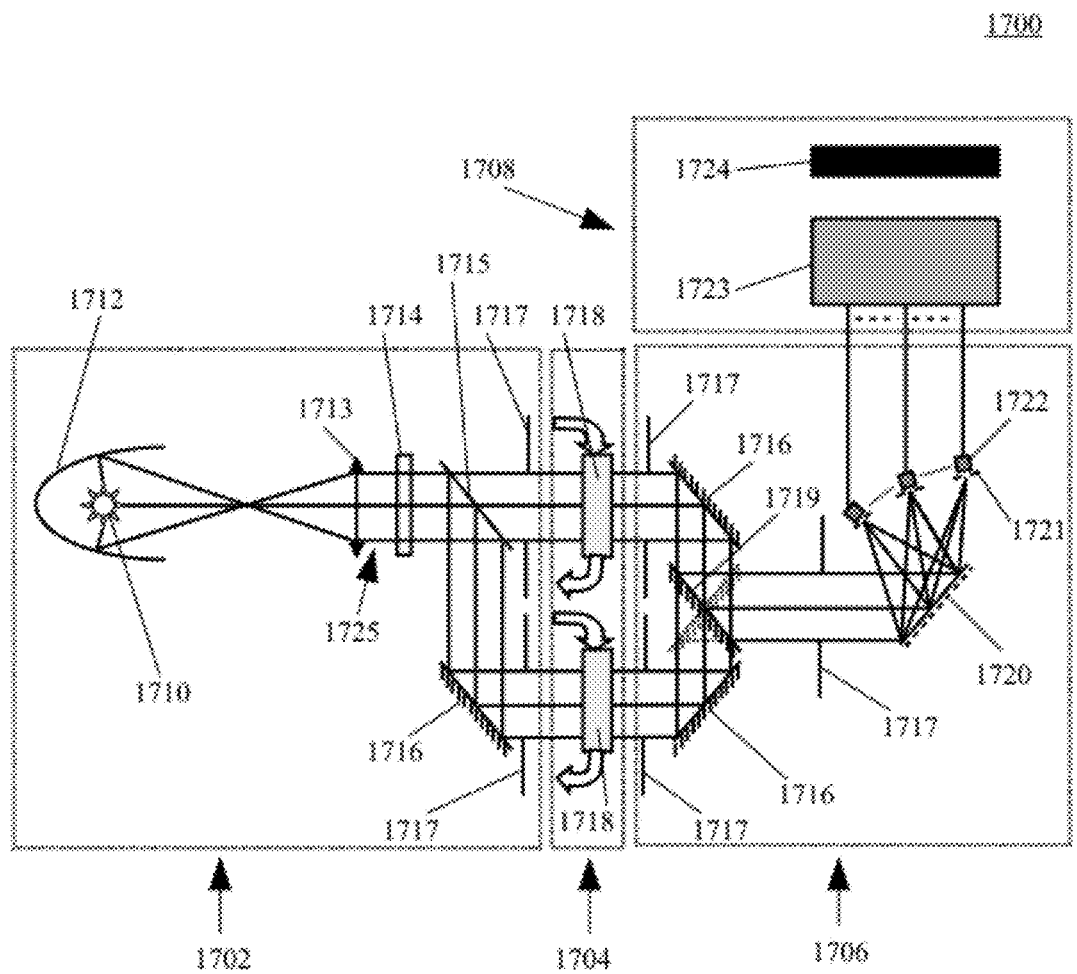
FIG. 17 shows FIG. 2 from U.S. patent application Ser. No. 11/744,643 (which was incorporated by reference), as an example for the optical unit.

FIG. 17 shows FIG. 2 from U.S. patent application Ser. No. 11/744,643 (which was incorporated by reference), as an example embodiment of the optical unit. This optical unit comprises a system 1700 for measuring the absorption of electromagnetic radiation by Hb derivatives in biological samples. The system 1700 includes light block 1702, sample block 1704, detection block 1706, and signal processing block 1708.

Light block 1702 further includes a power supply (not shown) connected to light source 1710. Light source 1710 emits light in the ultraviolet and visible ranges of the electromagnetic spectrum. Focusing mirror 1712 partially surrounds light source 1710 and focuses the light so that the incident beam 1725 of light is directed to collimating optics system 1713. Optics system 1713 directs the rays of light so that the rays are parallel to each other, and are directed toward filters 1714. Filter 1714 block light in spectral regions such as short to medium range ultraviolet and infrared that are not used in the analysis. In one embodiment, light block 1702 includes beam splitter 1715, mirrors 1716, and one or more exit and entry slits 1717. These devices direct the light beam into two separate, parallel paths as it passes into sample block 1704.

Sample block 1704 provides a device to introduce the sample to be analyzed into the path of incident light beam 1725. In one embodiment of the invention, sample block 1704 includes one or more quartz cuvettes or blood transfusion tubes, and a bracket that holds the cuvettes or transfusion tubes securely in the path of light beam 1725. In one embodiment of the invention, the cuvettes or transfusion tubes provide a sample thickness of 0.05-0.5 mm. The required sample thickness is determined by the hematocrit. In another embodiment, two fiber optic guides are placed in the optical contact, and a small amount of sample is placed between the guides. This arrangement allows the sample thickness to be optimized by the position of the fiber optic guides relative to each other during the analysis. In another embodiment, sample block 1704 includes one or more flow through cuvettes 1718. In another embodiment, the portion of flow through cuvette 1718 that is situated in light beam 1725 is surrounded by an integration sphere. As shown in FIG. 17, incident light beam 1725 is split by beam splitter 1715, and is directed so that one portion of the incident light beam 1725 passes through each of two flow through cuvettes 1718 and into detection block 1706. In one embodiment, detection block 1706 analyzes each beam alternatingly, allowing for rapid analysis and comparison of the two beams.

Detection block 1706 includes entry and exit slits 1717 coupled with mirrors 1716, that together focus the light beam on turning mirror 1719, which in turn, directs the light beam to a dispersion element that disperses light of different wavelengths over a defined area. In one embodiment, the dispersion element is diffraction grating 1720. In another embodiment, the light is focused by either the diffraction grating 1720 or another focusing element and the detector 1722 is positioned at the focal point of light at each wavelength of interest. In one embodiment, the diffracted light falls on a series of slits 1721 that are arranged so that light having the wavelength of interest passes through slits 1721 and impinges on detectors 1722. detectors 1722 generate a signal in response to the received light and send the signal to signal processing block 1708.

Signal processing block 1708 includes signal amplifiers, and appropriate logic circuits for signal correction 1723, to produce and record signal 1724. In one embodiment of the invention, signal amplitudes are processed using multi-wavelength analysis algorithms. In another embodiment, a dedicated, programmed, processor is employed. In yet another embodiment, the signals are analyzed externally in a computer using appropriate software programs.

Figure 18:
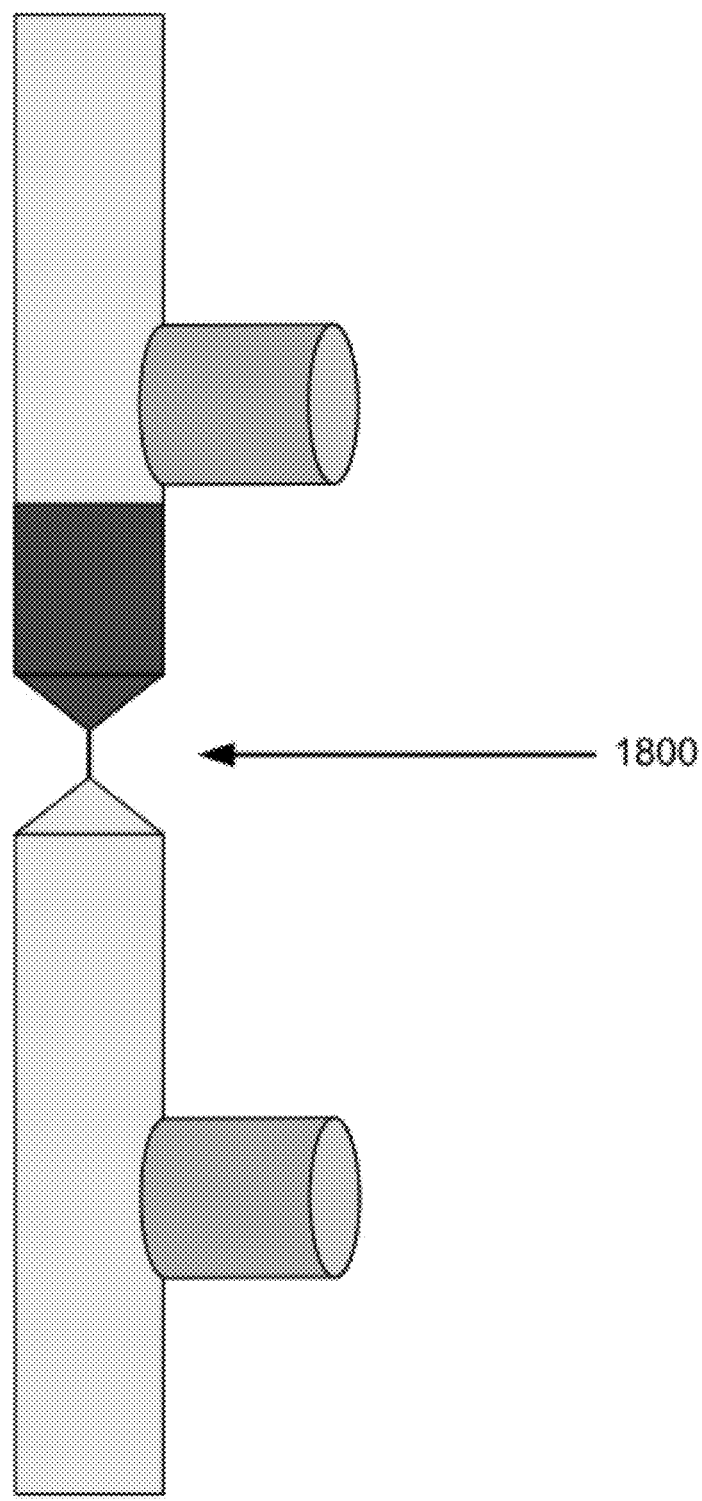
FIG. 18 shows a capillary-tube as an example for the hemolysis unit.

FIG. 18 shows a capillary-tube 1800 as an example embodiment of the hemolysis unit.

Figure 19:
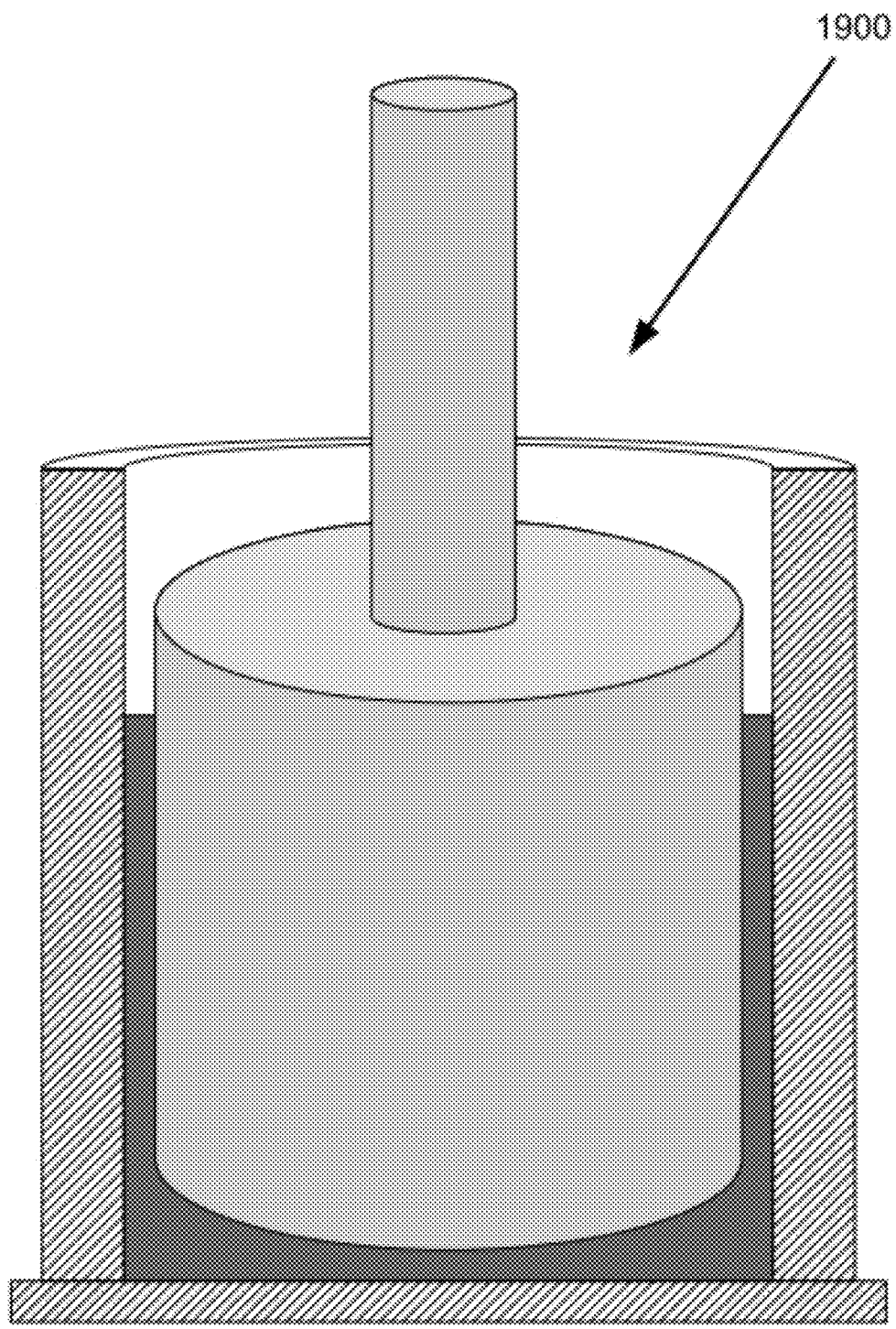
FIG. 19 shows concentric cylinders as an example for the hemolysis unit.

FIG. 19 shows concentric-cylinders 1900 as an example embodiment of the hemolysis unit.

Figure 20:
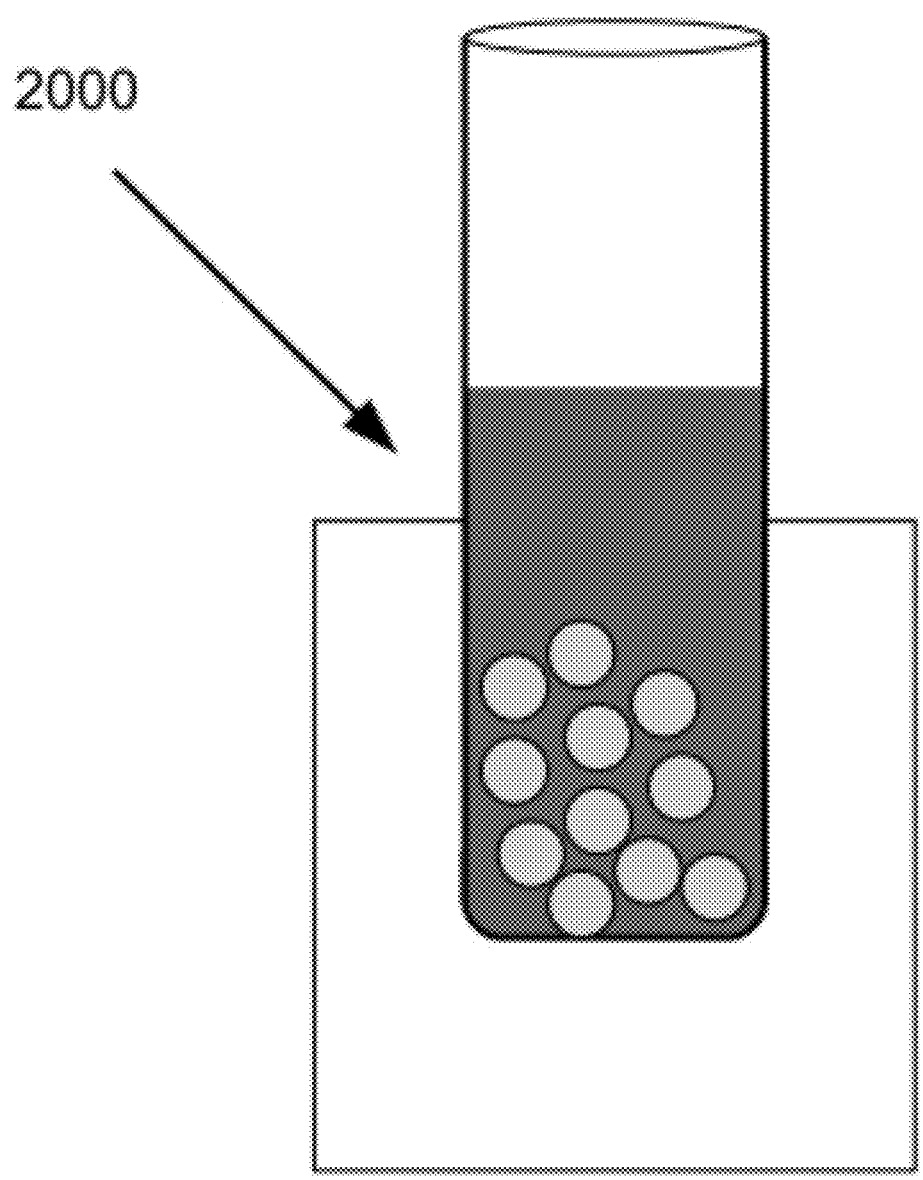
FIG. 20 shows a bead mill as an example for the hemolysis unit.

FIG. 20 shows a bead-mill 2000 as an example embodiment of the hemolysis unit.

Figure 21:
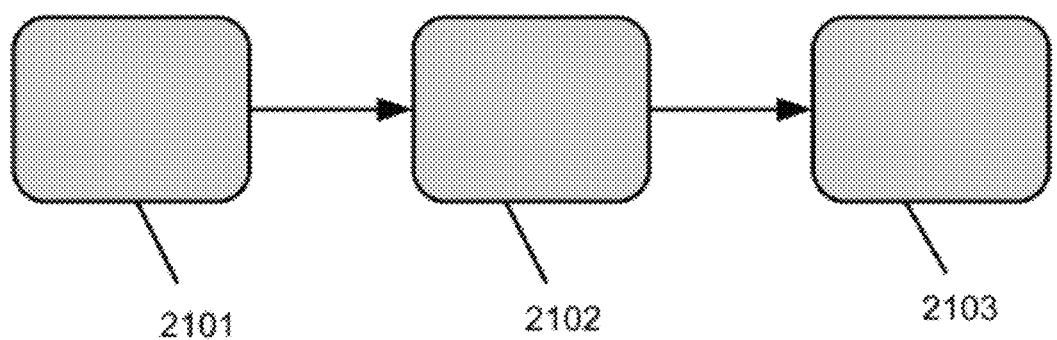
FIG. 21 shows a generalized system block diagram including a hemolysis unit, an optical unit, and a computation unit.

FIG. 21 shows a system block diagram including a generalized computation unit 2103, for processing the data obtained from an optical unit 2102, as the hemolysis gets caused by a hemolysis unit 2101.

Two clear hurdles remain before general acceptance of this testing would be attained. First, extensive in vitro trials must be performed to confirm the time-independent aspect of RBC degradation, as reflected by membrane fragility. Secondly, in vivo clinical trials will be needed to link measured RBC fragility with relevant clinical outcomes. The link could be challenging to definitively establish, as there is not yet an accepted "gold standard" for transfusion efficacy. Selection of the proper performance metric(s) and appropriate patient groups will require continued collaboration and consultation with multiple blood bankers and clinicians. Despite the complexity and scope of the undertaking, there is indeed precedent for such studies ultimately achieving broad acceptance (e.g. TRICC Trial).

The expected regulatory hurdles are minor, as no patient contact or product alterations are involved, and no patient would receive anything not already approved under current protocols. In the future, it is conceivable that the 42-day maximum shelf life could be replaced altogether by real-time quality tracking based on anticipated blood viability (e.g. through RBC fragility testing) and other tests as necessary to ascertain blood quality, but initially the testing will simply improve utilization of blood presently being allocated on a FIFO or random basis.

Blood products are valuable and scarce resources, and all efforts must be made to maximize their availability and efficacy. While the need to store RBC remains unavoidable at this time, steps can and should be taken to minimize net quality loss and increase the utilization of all blood supply. A simple, affordable test of RBC fragility properties as an aggregate quality-loss metric would aid medical professionals in making informed decisions regarding RBC release, selection, and use.

For the purposes of this disclosure, blood is defined as whole blood or packed red blood cells.

For the purposes of this disclosure, cell free hemoglobin is defined as hemoglobin released into blood plasma or RBC storage solution from erythrocytes.

For the purposes of this disclosure, hemoglobin is defined as various forms of hemoglobin including, but not limited to, oxygenated-, deoxygenated-, carboxy-, and methoxy-forms of hemoglobin as well as total hemoglobin taken as an aggregate of all its forms.

For the purposes of this disclosure, triage is defined as prioritizing medical resources based on relative patient need.

For the purposes of this disclosure, erythrocyte, also known as a red blood cell, is a blood cell containing hemoglobin and responsible for oxygen delivery to body tissues. The capitalized term Red Blood Cell, or RBC, is the proper name for erythrocytes in storage solution used in transfusion medicine.

While the present invention has been described herein with reference to an embodiment and various alternatives thereto, it should be apparent that the invention is not limited to such embodiments. Rather, many variations would be apparent to persons of skill in the art without departing from the scope and spirit of the invention, as defined herein and in the claims.

We claim:

1. An apparatus for assessing quality of specific units of stored blood product, comprising:
    a hemolysis unit configured to apply controlled physical stress to a sample containing red blood cells, said stress being applicable at one or more combination(s) of intensity and duration, for causing hemolysis of at least a portion of said cells;
    an optical analysis unit configured to optically evaluate said hemolysis to create one or more data point(s) corresponding to said one or more combination(s) of intensity and duration, whereby each data point reflects what fraction of cells became hemolysed upon having the stress applied for a given duration at a given intensity; and
    a computation unit configured to generate from said data point(s) a representation of quality for a specific unit of blood product, said representation of quality based on a correlation of in vitro blood cell fragility data to red blood cell degradation during storage.

2. The apparatus of claim 1, wherein said optical unit comprises a system for determining cell-free hemoglobin concentration within a sample containing at least one cell-free hemoglobin derivative and at least one cellular hemoglobin derivatives contained within erythrocytes, the system comprising:
    a light source configured to emit light;
    a sample block containing the sample and configured to allow the light to pass through the sample wherein, a first portion of the light, having a wavelength of about 390-460 nm, is absorbed by the cell-free hemoglobin derivatives, and a second portion of the light, having a wavelength of about 390-460 nm, is absorbed by the cellular hemoglobin derivatives contained within erythrocytes;
    at least one absorption detector configured to determine the light absorption of the sample block containing the sample, within a wavelength range of about 390-460 nm, and to generate a flattened spectra of cellular hemoglobin derivatives contained within erythrocytes and a non-flattened spectra of cell-free hemoglobin derivatives; and
    a processor configured to use data from the absorption detector to compare the flattened spectra of cellular hemoglobin derivatives contained within erythrocytes to the non-flattened spectra of cell free hemoglobin derivatives determined from the change in the light absorption of the sample within a wavelength range of 390-460 nm, and thereby determine the cell free hemoglobin concentration within the sample, said processor being either said computation unit or a separate unit.

3. The apparatus of claim 1, wherein said controlled physical stress comprises mechanical stress.

4. The apparatus of claim 3, wherein said hemolysis unit comprises a capillary through which pressure drives said sample.

5. The apparatus of claim 3, wherein said hemolysis unit comprises concentric cylinders, with an inner cylinder rotating to provide cell-wall interaction stress to red blood cells residing in a gap between said inner cylinder and an outer cylinder.

6. The apparatus of claim 3, wherein said hemolysis unit comprises a bead mill.

7. The apparatus of claim 1, wherein said data point(s) comprise a profile which has multiple data points representing what fraction of cells became hemolysed under particular stress conditions.

8. The apparatus of claims 1, further comprising a disposable single-use component configured to be able to contain said sample while said hemolysis unit applies said stress.

9. The apparatus of claim 1, wherein said representation of quality is a representation of anticipated future quality.

10. The apparatus of claim 1, wherein said representation of quality combines red blood cell fragility with morphologic parameters, metabolic parameters, age, or some combination thereof in characterizing blood product.

11. The apparatus of claim 7, wherein said representation of quality is a value interpolated from said profile, said value reflecting an inference of what level of stress intensity or duration is required to lyse a particular fraction of said cells.

12. The apparatus of claim 7, wherein said stress conditions can vary by duration while intensity remains essentially uniform for all of said combination(s), and wherein levels of said duration can be quantified, and wherein said representation of quality is a two-dimensional curve or a set of paired values based on said profile, said two-dimensional curve or set of paired values reflecting dependency of hemolysis upon stress duration.

13. The apparatus of claim 7, wherein said stress conditions can vary by both intensity and duration, and wherein said representation of quality is a three-dimensional curve(s) or matrix based on said profile, said three-dimensional curve(s) or matrix reflecting dependency of hemolysis upon both stress intensity and stress duration.

14. The apparatus of claim 1, wherein a particular duration of stress can be accomplished by multiple discrete iterations of applied stress.

15. The apparatus of claim 1, wherein discrete portions of the sample are separately subjectable to stress.

16. The apparatus of claim 1, wherein said optical unit comprises a spectrophotometer configured to measure light absorption.

* * * * *